(12) United States Patent
Rigante et al.

(10) Patent No.: US 9,570,288 B2
(45) Date of Patent: Feb. 14, 2017

(54) METHOD TO FABRICATE FINFET SENSORS, IN PARTICULAR, FINFET SENSORS FOR IONIC, CHEMICAL AND BIOLOGICAL APPLICATIONS ON SI-BULK

(71) Applicant: ECOLE POLYTECHNIQUE FEDERALE DE LAUSANNE (EPFL), Lausanne (CH)

(72) Inventors: Sara Rigante, Renens (CH); Adrian Mihai Ionescu, Ecublens VD (CH)

(73) Assignee: ECOLE POLYTECHNIQUE FEDERALE DE LAUSANNE (EPFL) (CH)

( * ) Notice: Subject to any disclaimer, the term of this patent is extended or adjusted under 35 U.S.C. 154(b) by 0 days.

(21) Appl. No.: 14/219,261

(22) Filed: Mar. 19, 2014

(65) Prior Publication Data

US 2015/0268189 A1    Sep. 24, 2015

(51) Int. Cl.
*H01L 21/02*     (2006.01)
*H01L 29/66*     (2006.01)
(Continued)

(52) U.S. Cl.
CPC ..... *H01L 21/02238* (2013.01); *G01N 27/4146* (2013.01); *H01L 21/3081* (2013.01);
(Continued)

(58) Field of Classification Search
CPC .............. G01N 27/414; H01L 29/6653; H01L 21/02238; H01L 29/7851; H01L 21/30604; H01L 29/66795; H01L 29/16
See application file for complete search history.

(56) References Cited

U.S. PATENT DOCUMENTS

2004/0150029 A1*  8/2004  Lee ................... H01L 29/41791
                                                                                                257/308
2005/0250279 A1*  11/2005  Son ................. H01L 21/823481
                                                                                                438/216
(Continued)

OTHER PUBLICATIONS

"Ion Sensitive Field-Effect Transistor—ISFET," Microsens SA, 2007, 4 pages. Retrieved from: www.microsens.ch/products/chemical.htm.
(Continued)

*Primary Examiner* — Michelle Mandala
(74) *Attorney, Agent, or Firm* — Sheridan Ross P.C.

(57) ABSTRACT

The present invention relates to a method of producing a FinFET sensor device comprising the steps of:
  providing a silicon substrate;
  etching the silicon substrate to produce at least one upwardly extending Fin structure externally protruding from a surface of the silicon substrate;
  depositing a spacer layer on the at least one Fin structure;
  anisotropically etching a section of the spacer layer to expose the underlying silicon;
  isotropic etching of the exposed silicon surrounding the at least one Fin structure; and
  carrying out oxidation of the silicon surrounding the at least one Fin structure to produce a Fin structure of silicon inside the at least one Fin structure.
The present invention also relates to FinFET sensor devices produced by the above method.

17 Claims, 33 Drawing Sheets

Figure 4:
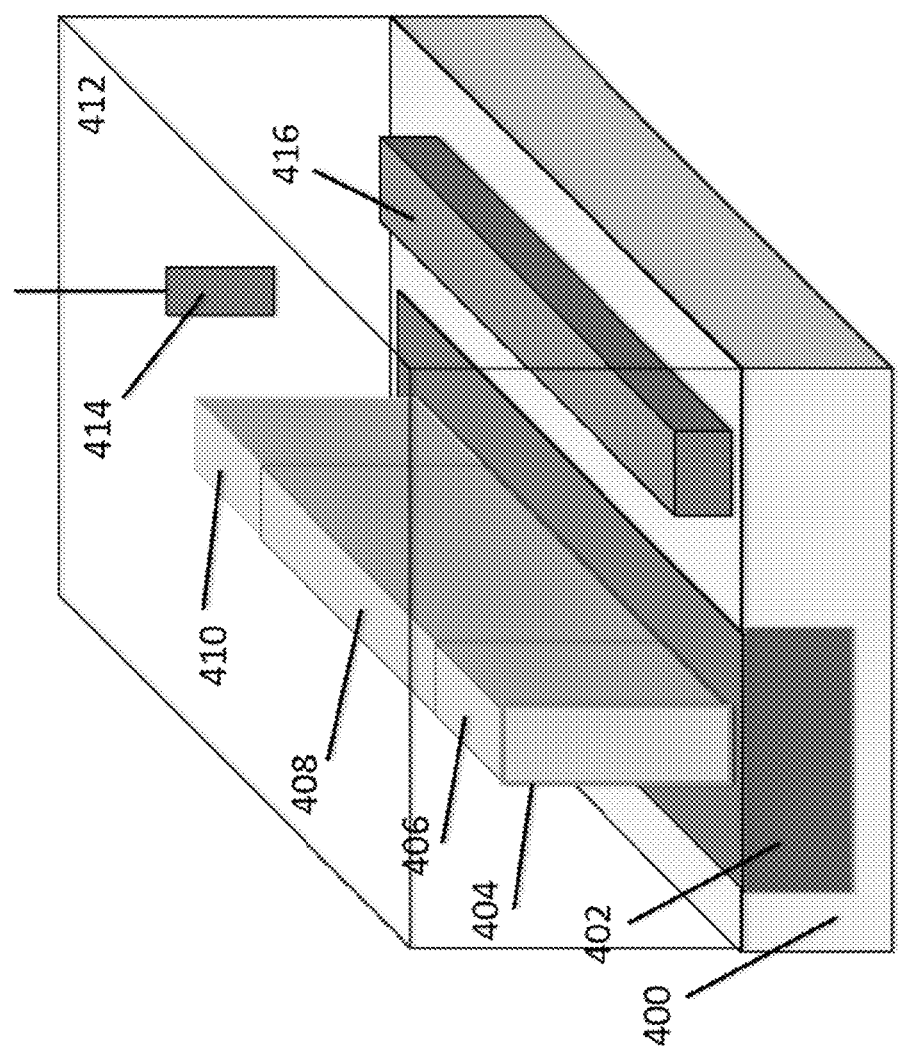

(51) Int. Cl.
  *H01L 29/78* (2006.01)
  *H01L 21/308* (2006.01)
  *H01L 21/311* (2006.01)
  *G01N 27/414* (2006.01)
(52) U.S. Cl.
  CPC .... *H01L 21/3086* (2013.01); *H01L 21/31116* (2013.01); *H01L 29/6653* (2013.01); *H01L 29/66795* (2013.01); *H01L 29/7851* (2013.01); *G01N 27/4145* (2013.01)

(56) References Cited

U.S. PATENT DOCUMENTS

| | | | | |
|---|---|---|---|---|
| 2009/0278196 | A1* | 11/2009 | Chang | H01L 21/823412 257/328 |
| 2011/0049599 | A1* | 3/2011 | Taketani | H01L 21/823431 257/302 |
| 2015/0021690 | A1* | 1/2015 | Jacob | H01L 27/0886 257/347 |

OTHER PUBLICATIONS

Abe et al., "ISFET's using inorganic gate thin films," IEEE Transactions on Electron Devices, 1979, vol. 26, No. 12, pp. 1939-1944.
Ahn et al., "A pH sensor with a double-gate silicon nanowire field-effect transistor," Applied Physics Letters, 2013, vol. 102, Iss. 8, pp. 083701-1-083701-5.
Ahn et al., "Nanowire FET Biosensors on a Bulk Silicon Substrate," IEEE Transactions on Electron Devices, 2012, vol. 59, No. 8, pp. 2243-2249.
Bergveld, "Thirty years of ISFETOLOGY—What happened in the past 30 years and what may happenin the next 30 years," Sensors and Actuators B, 2003, vol. 88, pp. 1-20.
Brehm-Stecher et al., "Single-Cell Microbiology: Tools, Technologies, and Applications," Microbiology and Molecular Biology Reviews, 2004, vol. 68, No. 3, pp. 538-559.
Chen et al., "Silicon-based nanoelectronic field-effect pH sensor with local gate control," Applied Physics Letters, 2006, vol. 89, Iss. 22, pp. 223512-1-223512-3.
Chiang et al., "Nanowire Transistor-Based Ultrasensitive Virus Detection with Reversible Surface Functionalization," Chemistry—An Asian Journal, 2012, vol. 7, Iss. 9, pp. 2073-2079.
Cobbe et al., "Continuous coronary sinus and arterial pH monitoring during pacing-induced ischaemia in coronary artery disease," British Heart Journal, 1982, vol. 47, No. 4, pp. 369-374.
Colinge, "Chapter 1—The SOI MOSFET: from Single Gate to Multigate," *FinFETs and OtherMulti-Gate Transistors*, Springer US, 2008, pp. 1-48.
Colinge, "Chapter 5—The SOI MOSFET," *Silicon-On-Insulator Technology: Materials to VLSI, 2nd Edition*, Kluwar Acedemic Publishers, 1997, pp. 123-185.
Cui et al., "Nanowire Nanosensors for Highly Sensitive and Selective Detection of Biological and Chemical Species," Science, 2001, vol. 293, No. 5533, pp. 1289-1292.
Hahm et al., "Direct Ultrasensitive Electrical Detection of DNA and DNA Sequence Variations Using Nanowire Nanosensors," Nano Letters, 2004, vol. 4, No. 1, pp. 51-54.
Hisamoto et al., "A Fully Depleted Lean-channel Transistor (DELTA)—A novel vertical ultra thin SOI MOSFET," Technical Digest—International Electron Devices Meeting (IDEM '89), 1989, pp. 833-836.
Huang et al., "Sub 50-nm FinFET: PMOS," Technical Digest—International Electron Devices Meeting (IDEM '99), 1999, pp. 67-70.
Jin et al, "A rapid and efficient single-cell manipulation method for screening antigen-specific antibody-secreting cells from human peripheral blood," Nature Medicine, 2009, vol. 15, Iss. 9, pp. 1088-1092.

Kim et al., "Silicon nanowire ion sensitive field effect transistor with integrated Ag/AgCl electrode: pH sensing and noise characteristics," Analyst, 2011, vol. 136, pp. 5012-5016.
Kim et al., "Ultrasensitive, label-free, and real-time immunodetection using silicon field-effect transistors," Applied Physics Letters, 2007, vol. 91, No. 10, pp. 103901-1-103901-3.
Lacy et al., "Safety and tolerability of transoral Bravo capsule placement after transnasal manometry using a validated conversion factor," The American Journal of Gastroenterology, 2007, vol. 102, No. 1, pp. 24-32. (Abstract Only).
Law et al., "Semiconductor nanowires and nanotubes," Annual Review of Materials Research, 2004, vol. 34, pp. 83-122.
Lee et al., "Complementary Silicon Nanowire Hydrogen Ion Sensor With High Sensitivity and Voltage Output," IEEE Electron Device Letters, 2012, vol. 33, Iss. 12, pp. 1768-1770.
Lee et al., "Large-scale arrays of picolitre chambers for single-cell analysis of large cell populations," Lab on a Chip, 2010, vol. 10, pp. 2952-2958.
Li et al., "Complementary Detection of Prostate-Specific Antigen Using $In_2O_3$ Nanowires and Carbon Nanotubes," Journal of the American Chemical Society, 2005, vol. 127, No. 36, pp. 12484-12485.
Li et al., "Sequence-Specific Label-Free DNA Sensors Based on Silicon Nanowires," Nano Letters, 2004, vol. 4, No. 2, pp. 245-247.
Majumdar et al., "Chronic Acid-Related Disorders Are Common and Underinvestigated," The American Journal of Gastroenterology, 2003, vol. 98, No. 11, pp. 2409-2414.
Moore et al., "Progress in digital integrated electronics," International Electron Devices Meeting, 1975, vol. 21, pp. 11-13.
Oncescu et al., "Smartphone based health accessory for colorimetric detection of biomarkers in sweat and saliva," Lab on a Chip, 2013, vol. 13, pp. 3232-3238.
Pandolfino et al., "Acid reflux event detection using the Bravo wireless versus the Slimline catheter pH systems: why are the numbers so different?," Gut, 2005, vol. 54, No. 12, pp. 1687-1692.
Park et al., "Top-down fabricated silicon nanowire sensors for real-time chemical detection," Nanotechnology, 2010, vol. 21, No. 1, 9 pages.
Rigante et al., "FinFET integrated low-power circuits for enhanced sensing applications." Sensors and Actuators B: Chemical, vol. 186, 2013, pp. 789-795.
Rigante et al., "Finfet with fully PH-responsive $HFO_2$ as highly stable biochemical sensor," The 27th IEEE International Conference on Micro Electro Mechanical Systems (MEMS 2014), 2014, pp. 1063-1066.
Rigante et al., "High-k dielectric FinFETs towards sensing integrated circuits," 14th International Conference on Ultimate Integration on Silicon (ULIS), 2013, pp. 73-76.
Rigante et al., "Integrated FinFET based sensing in a liquid environment," The 17th International Conference on Proceedings of Solid-State Sensors, Actuators and Microsystems (Transducers Eurosensors XXVII), 2013, pp. 681-684.
Rigante et al., "Low Power FinFET pH-Sensor with High-Sensitivity Voltage Readout," Proceedings of the European Solid-State Device Research Conference (ESSDERC), 2013,4 pages.
Rigante et al., "Technological Development of High-k Dielectric FinFETs for Liquid Environment," no date, 9 pages.
Smith et al., "Clinical evaluation—continuous real-time intra-arterial blood gas monitoring during anesthesia and surgery by fiber optic sensor," International Journal of Clinical Monitoring and Computing, 1992, vol. 9, Iss. 1, pp. 45-52.
Stern et al., "Semiconducting Nanowire Field-Effect Transistor Biomolecular Sensors," IEEE Transactions on Electron Devices, 2008, vol. 55, No. 11, pp. 3119-3130.
Tamer et al., "The Levels of Sera Malondialdehyde, Erythrocyte Membrane $Na^+$-$K^+$/$Mg^{++}$ and $Ca^{++}$/$Mg^{++}$ Adenosine 5' Triphosphatase in Patients with Sickle Cell Anemia," Turkish Journal of Hematology, 2000, vol. 17, Iss. 1, pp. 23-26.
Tarasov et al., "Understanding the Electrolyte Background for Biochemical Sensing with Ion-Sensitive Field-Effect Transistors," ACS Nano, 2012, vol. 6, No. 10, pp. 9291-9298.

(56) References Cited

OTHER PUBLICATIONS

Tokimitsu et al., "Single Lymphocyte Analysis with a Microwell Array Chip," Cytometry Part A, 2007, vol. 71A, Iss. 12, pp. 1003-1010.
Vu et al., "Top-down processed silicon nanowire transistor arrays for biosensing," Physica Status Solidi A, 2009, vol. 206, No. 3, pp. 426-434.
Wang et al., "Label-free detection of small-molecule-protein interactions by using nanowire nanosensors," Proceedings of the National Academy of Sciences of the United States of America, 2005, vol. 102, No. 9, pp. 3208-3212.
Weinstein et al., "A new method for determining gastric acid output using a wireless pH-sensing capsule," Alimentary Pharmacology and Therapeutics, 2013, vol. 37, Iss. 12, pp. 1198-1209.
Wong et al., "Feasibility and tolerability of transnasal/per-oral placement of the wireless pH capsule vs. traditional 24-h oesophageal pH monitoring—a randomized trial," Alimentary Pharmacology and Therapeutics, 2005, vol. 21, Iss. 2, pp. 155-163.
Yoo et al., "Hydrogen Ion Sensing Using Schottky Contacted Silicon Nanowire FETs," IEEE Transactions on Nanotechnology, 2008, vol. 7, No. 6, pp. 745-748.
Zhang et al., "Highly sensitive measurements of PNA-DNA hybridization using oxide-etched silicon nanowire biosensors," Biosensors and Bioelectronics, 2008, vol. 23, Iss. 11, pp. 1701-1707.
Zhang et al., "Silicon nanowire biosensor for highly sensitive and rapid detection of Dengue virus," Sensors and Actuators B: Chemical, 2010, vol. 146, Iss. 1, pp. 138-144.
Zheng et al., "Multiplexed electrical detection of cancer markers with nanowire sensor arrays," Nature Biotechnology, 2005, vol. 23, No. 10, pp. 1294-1301.

\* cited by examiner

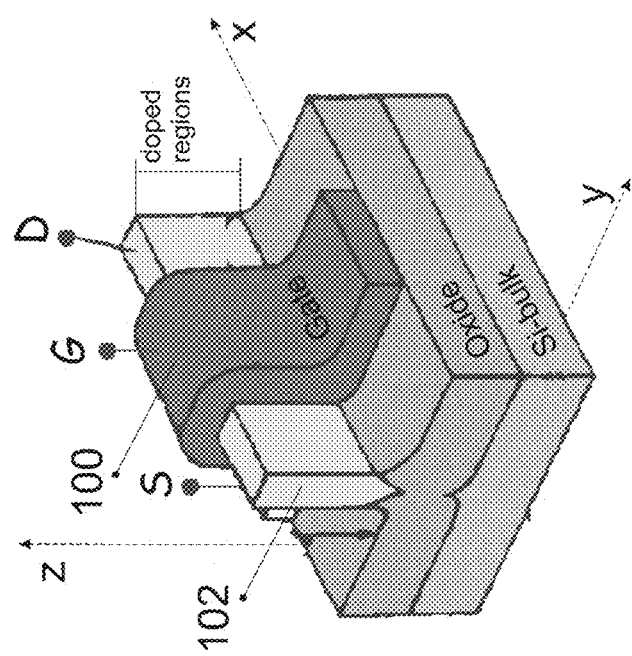
Figure1.A

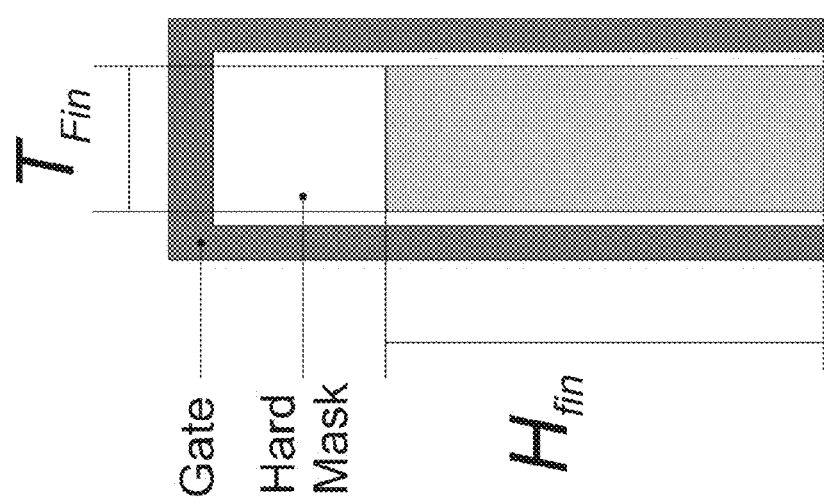
Figure1.B

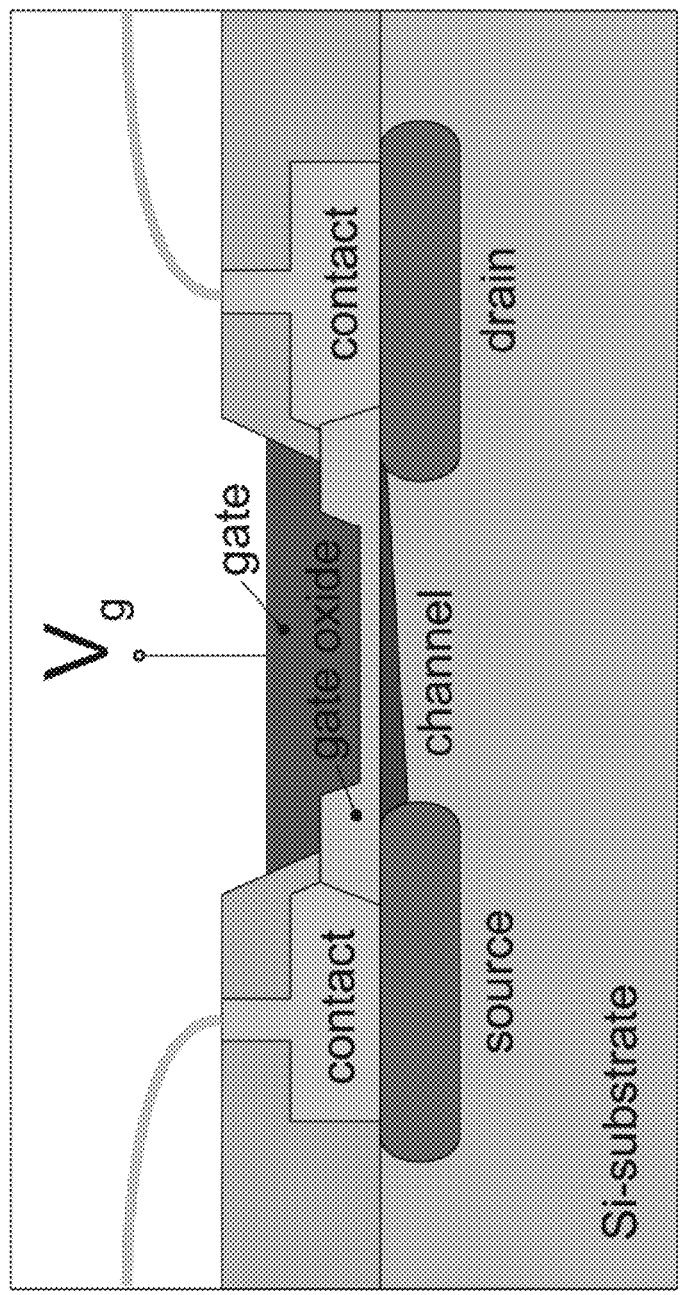
Figure 2.A

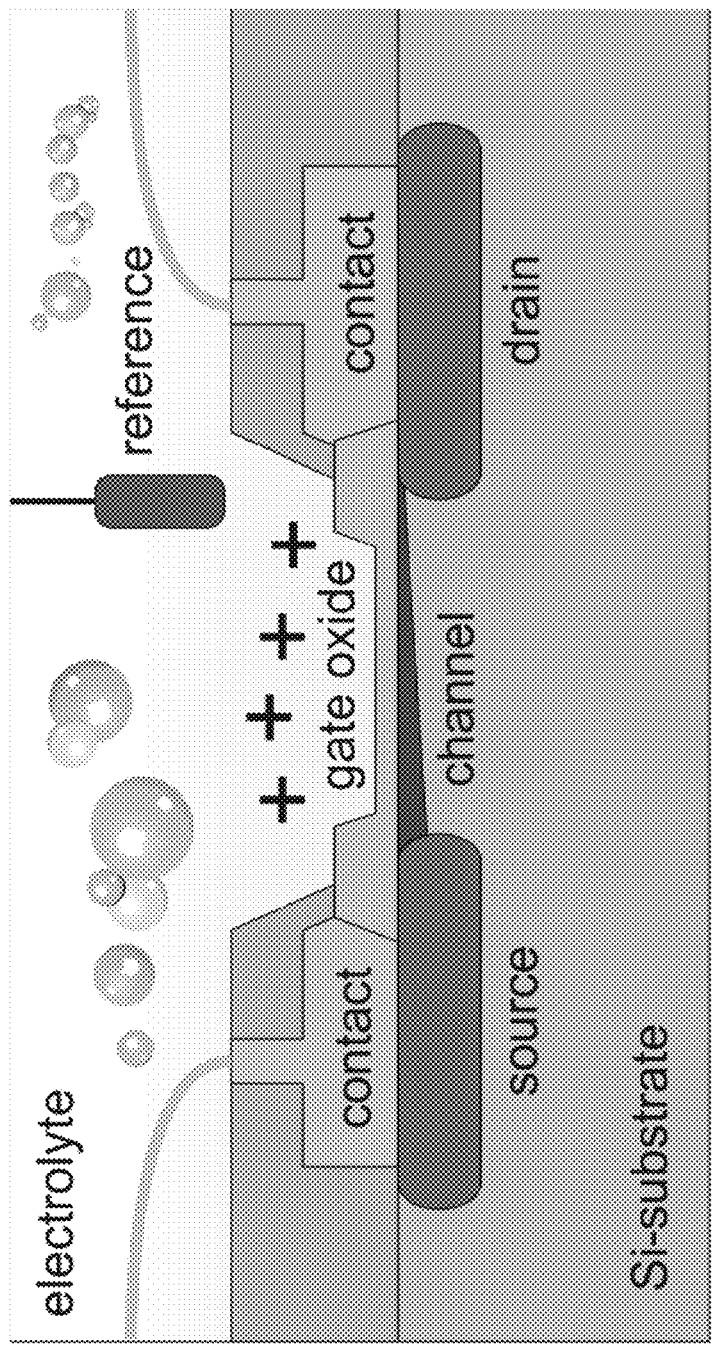
Figure 2.B

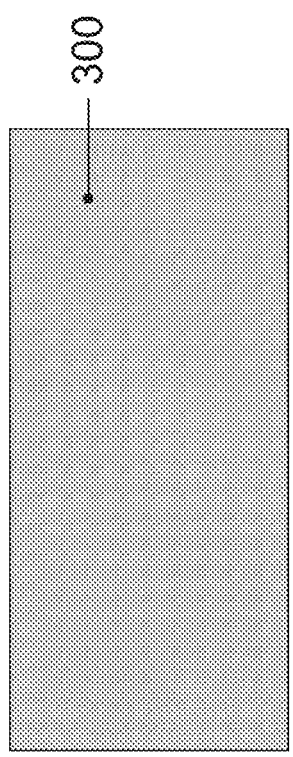
Figure 3.A
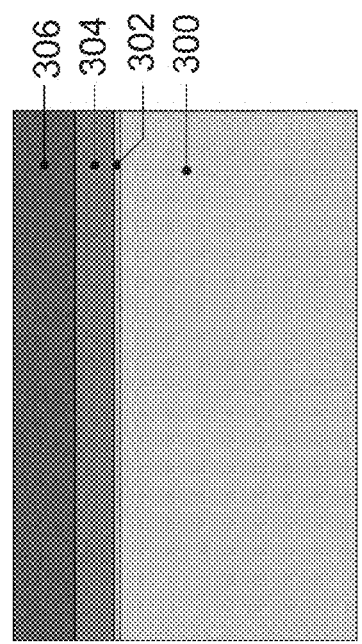
Figure 3.B

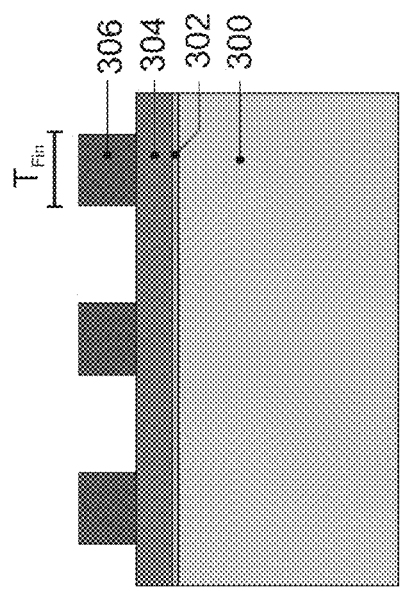
Figure 3.C
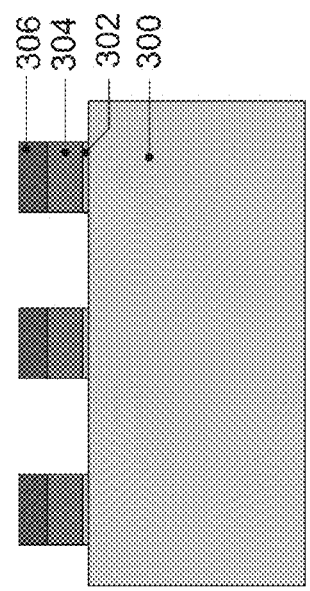
Figure 3.D

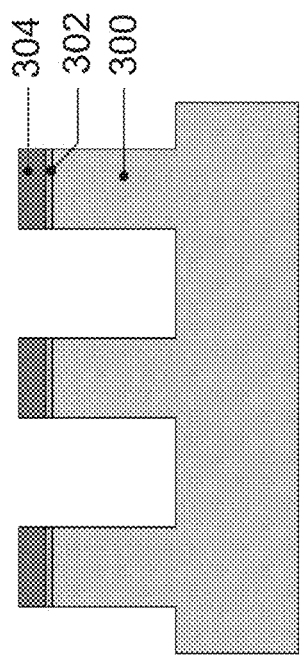
Figure 3.E
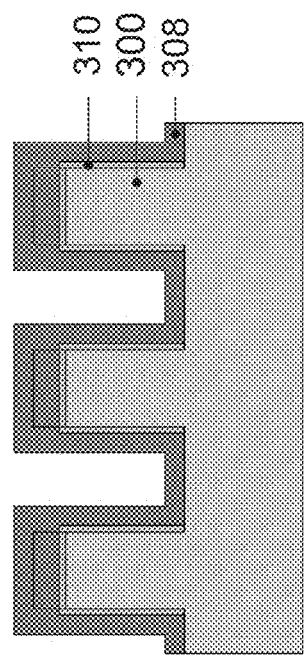
Figure 3.F

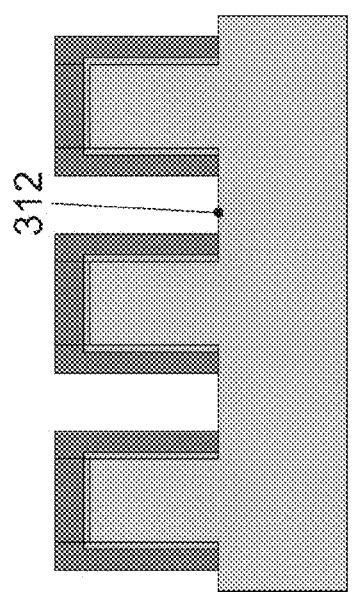
Figure 3.G
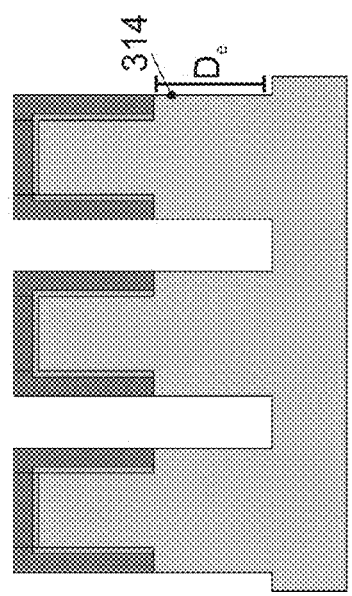
Figure 3.H

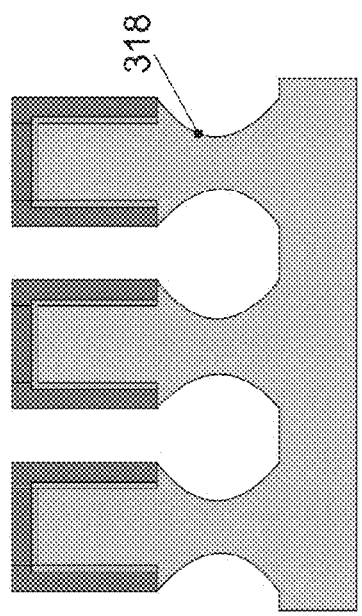
Figure 3.I
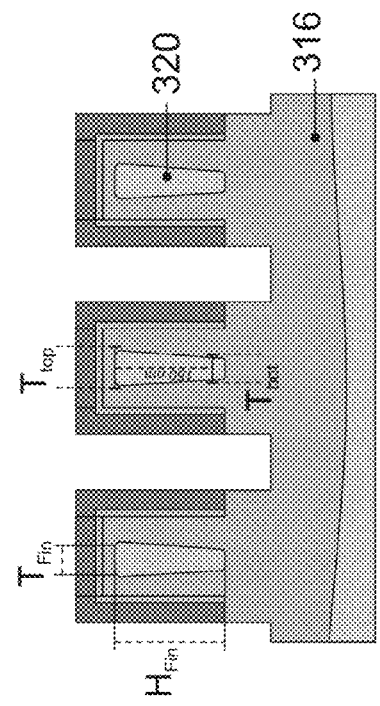
Figure 3.J

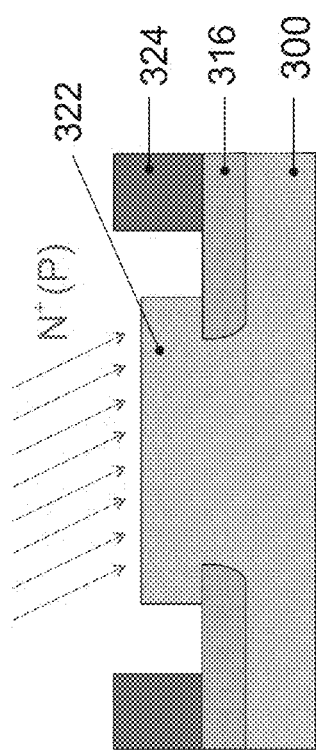
Figure 3.K
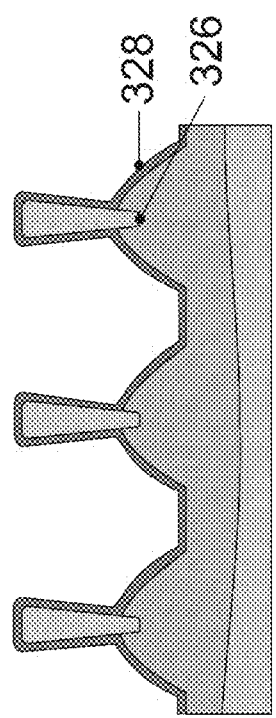
Figure 3.L

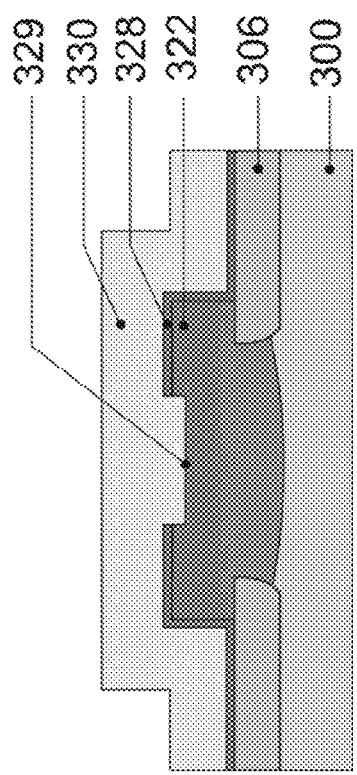
Figure 3.M
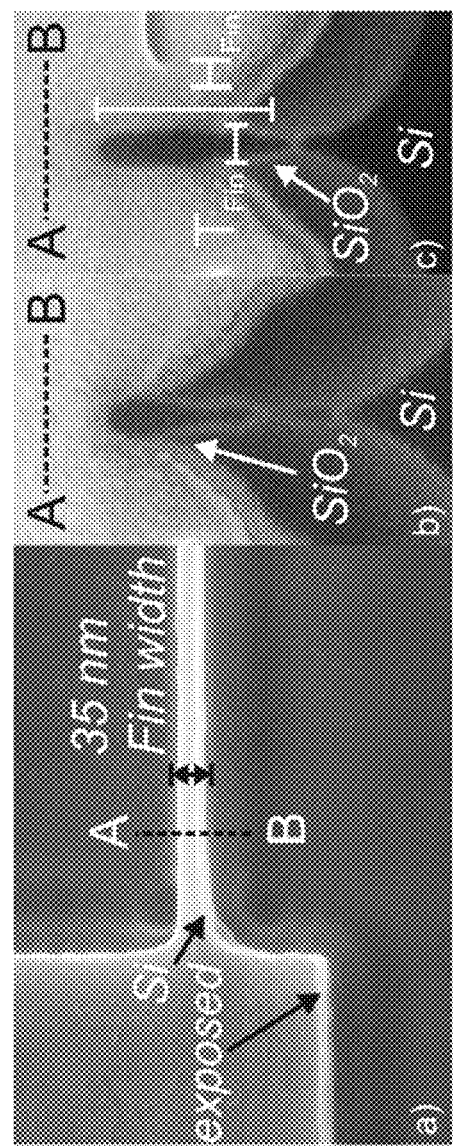
Figure 3.N

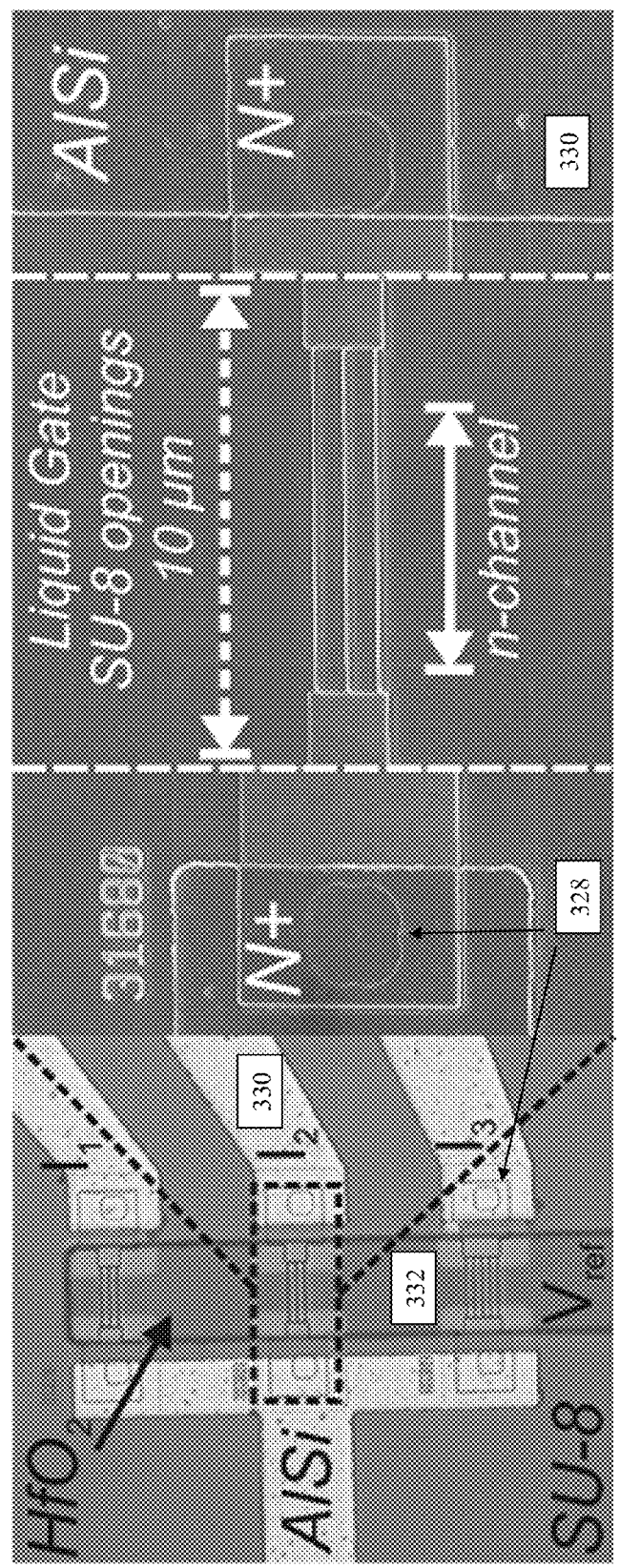
Figure 3.O

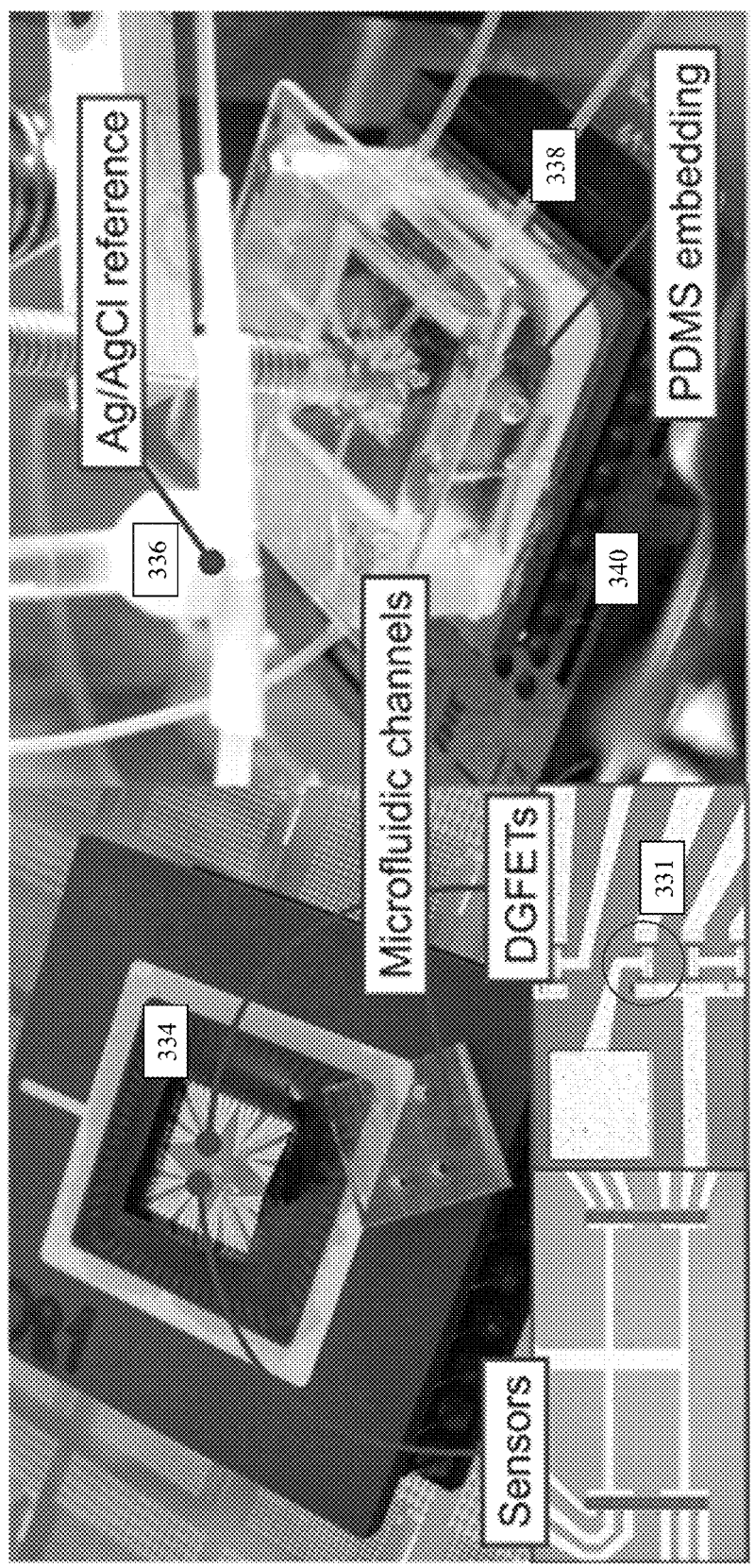
Figure 3.P

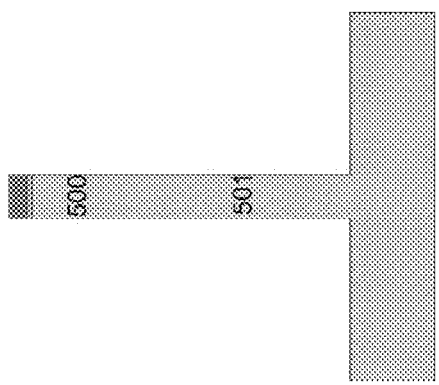
Figure 5.A
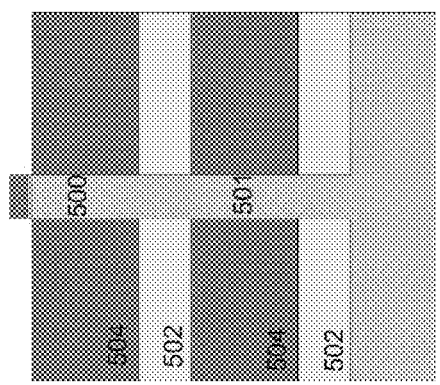
Figure 5.B

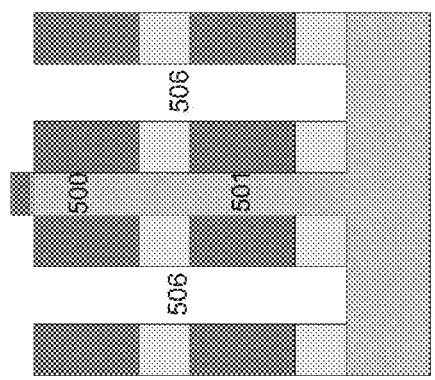
Figure 5.C
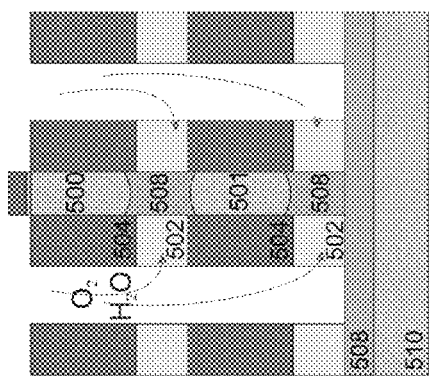
Figure 5.D

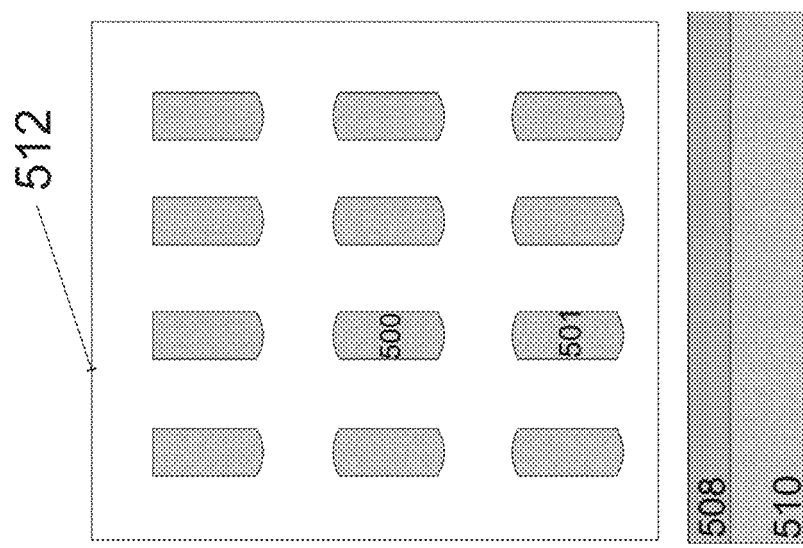
Figure 5.E

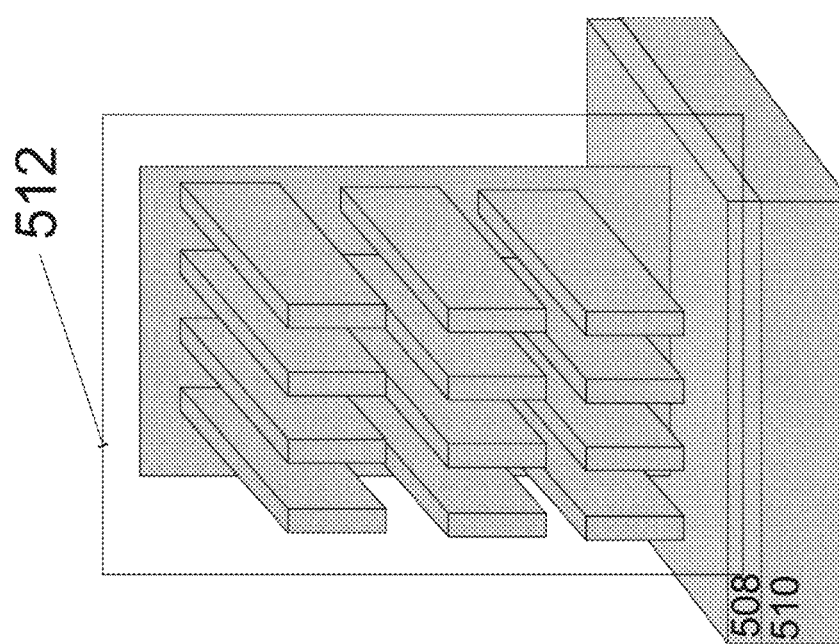
Figure 5.F

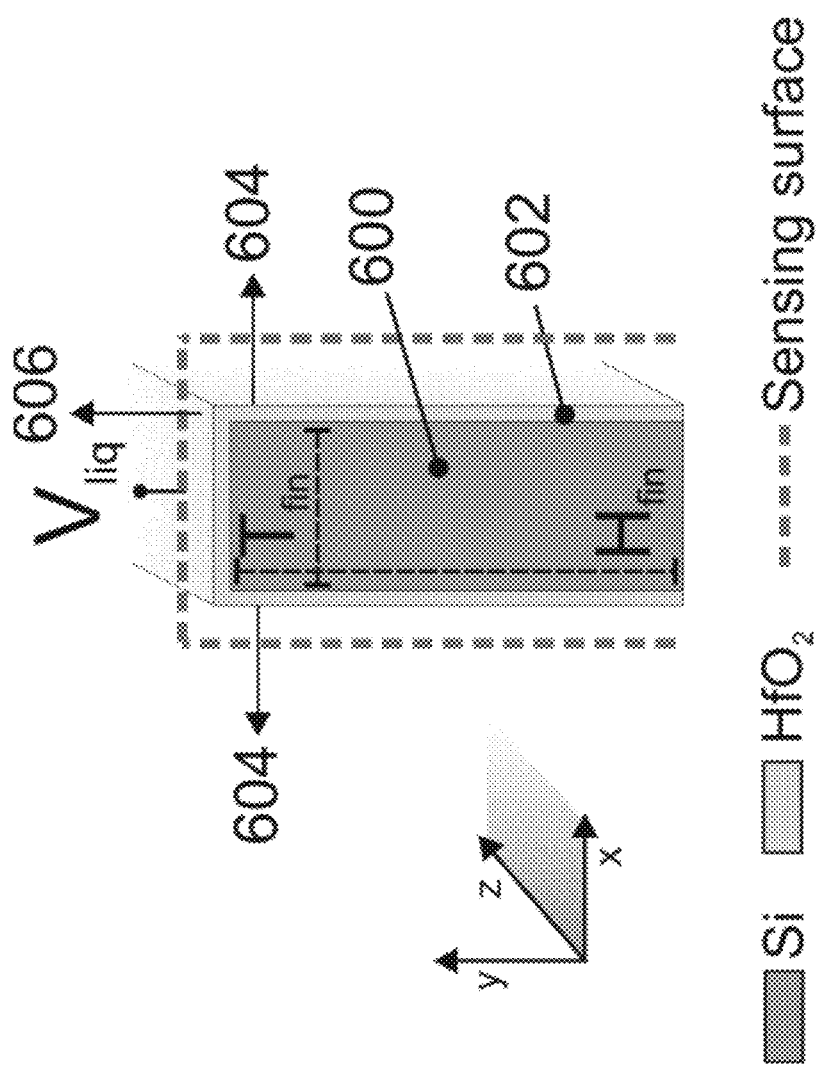
Figure 7.A

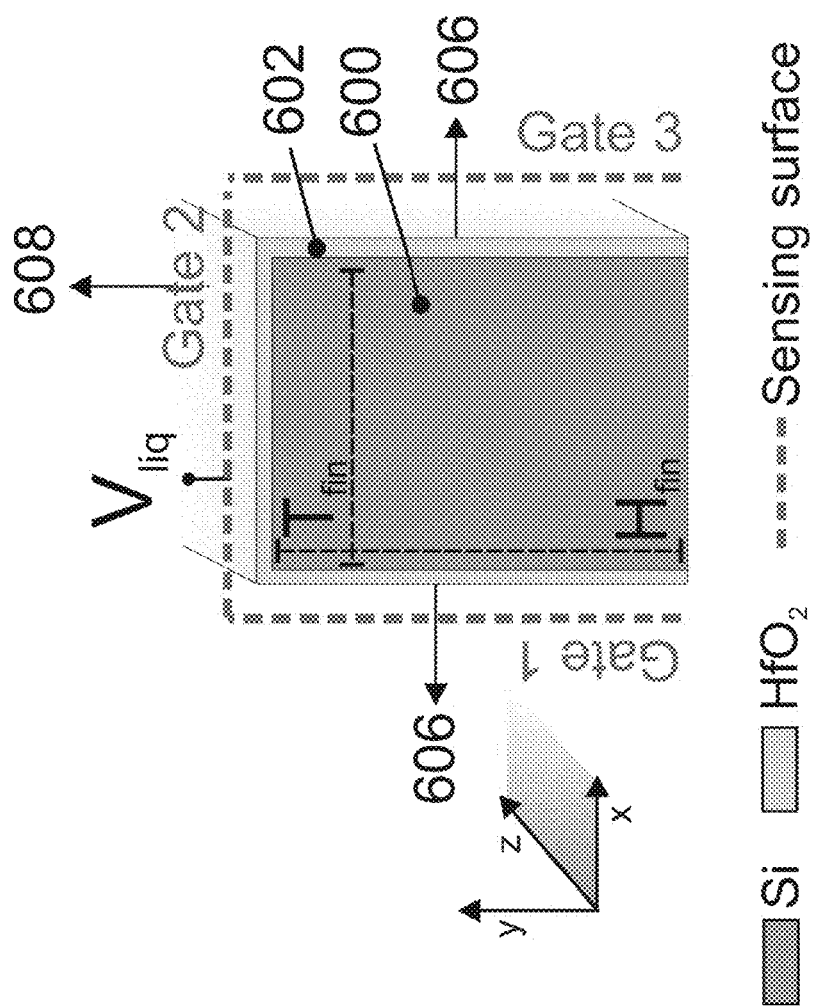
Figure 7.B

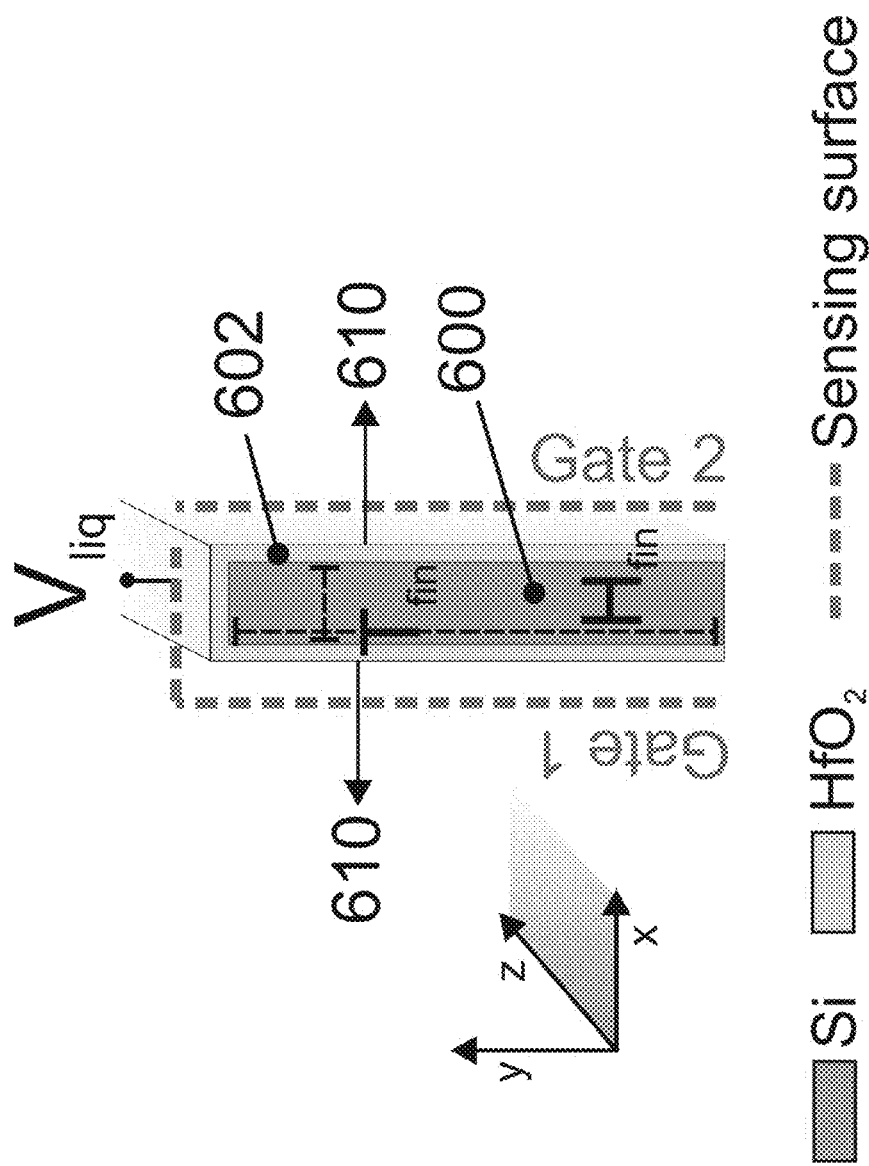
Figure 7.C

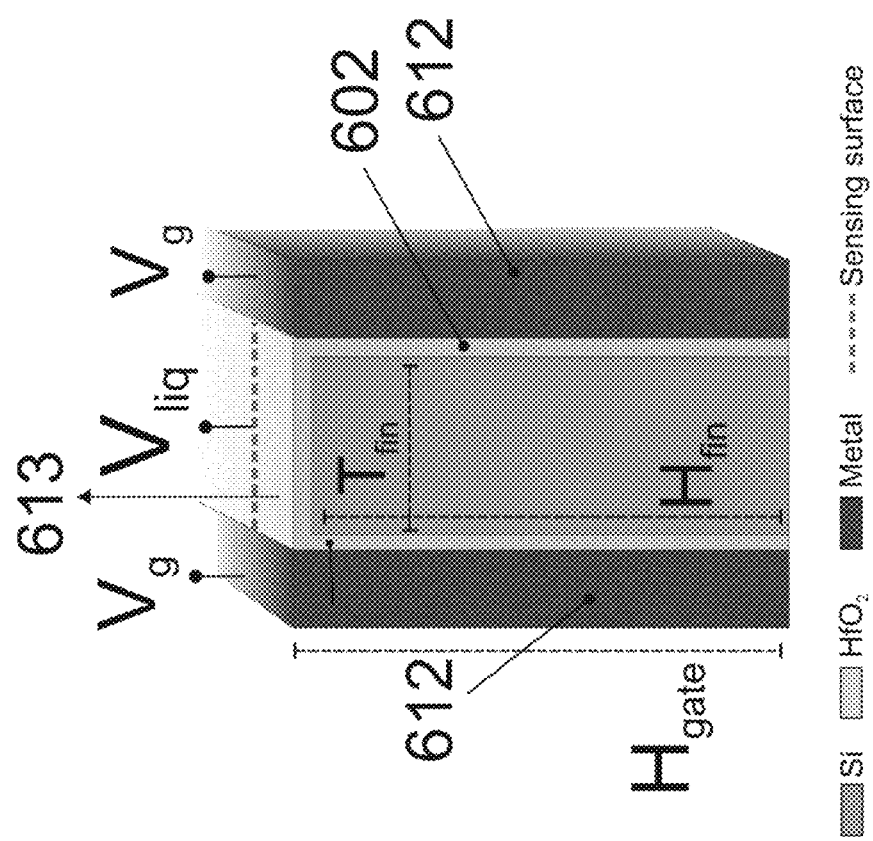
Figure 7.D

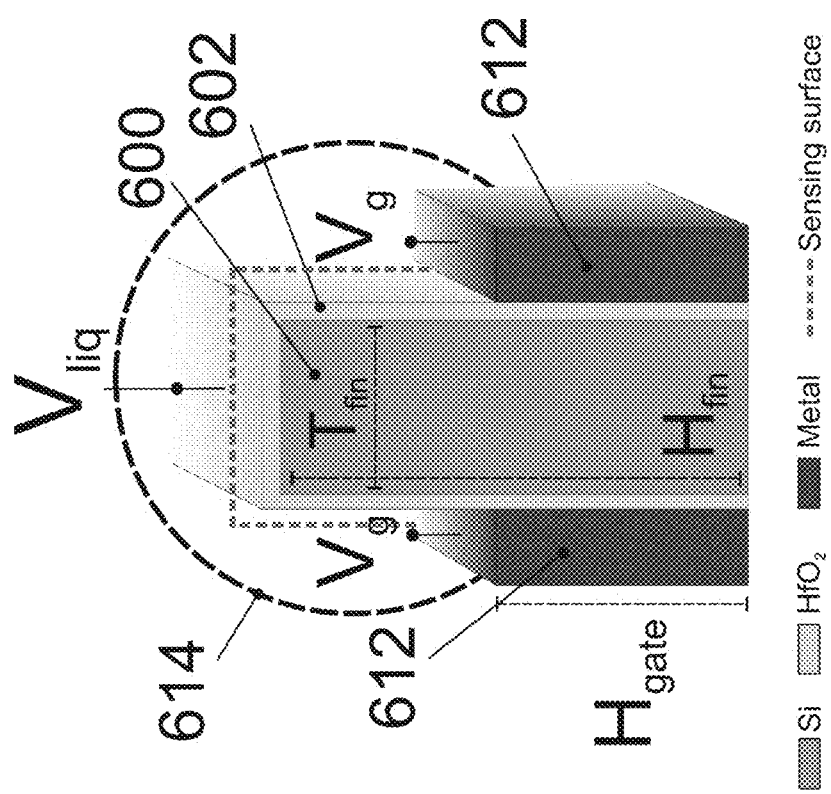
Figure 7.E

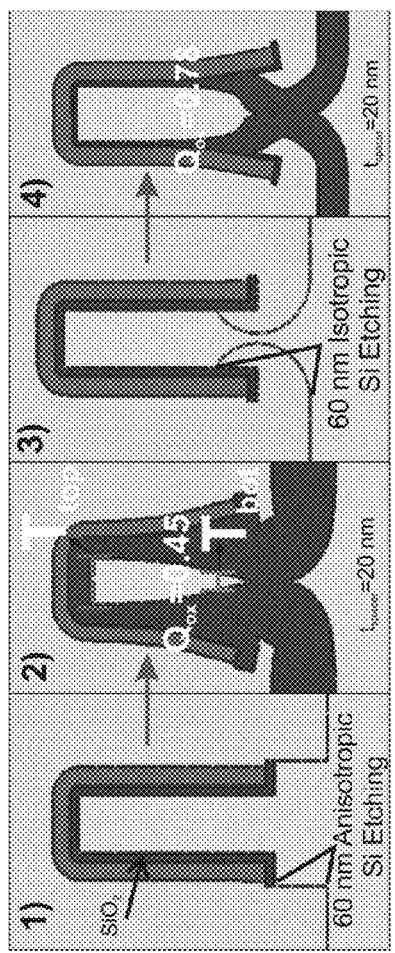
Figure 15.A
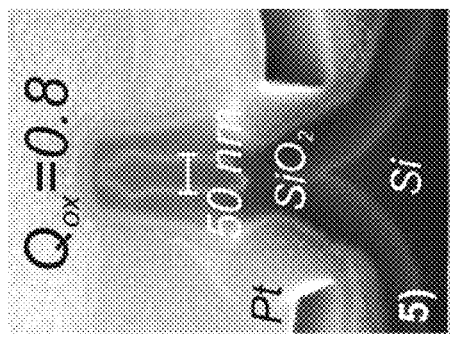
Figure 15.B

METHOD TO FABRICATE FINFET SENSORS, IN PARTICULAR, FINFET SENSORS FOR IONIC, CHEMICAL AND BIOLOGICAL APPLICATIONS ON SI-BULK

I. FIELD OF THE INVENTION

This invention concerns fabrication methods of Field Effect Transistor (FET) sensors for pH (H$^+$), chemical and biological detection and in particular FinFET sensors for pH (H$^+$), chemical and biological detection. The present invention also relates to FinFET sensors produced by such methods.

II. BACKGROUND OF THE INVENTION

FET Silicon Nanowires (SiNW) have emerged as promising candidates for a new generation of label-free real-time sensors [1] for the detection of chemical and biological species. Even though SiNWs' potential for sensing has been largely proven and the knowledge of sensing mechanisms widely extended, mass-production and integration of such sensors has still to face many challenges. This patent proposes an alternative sensor, able to provide better performance, especially in terms of stability and reliability. It also guarantees a direct integration with CMOS read-out electronics, preserving its performances upon scaling.

FinFET as State-of-the-Art Transistor:

The first fabricated non-planar FET was proposed in 1989 as "fully DEpleted Lean-channel TrAnsistor (DELTA)" by Hisamoto et al. [2], as illustrated in FIG. 1.A. The term FinFET was actually referring to the same DELTA structure but with an additional top hard-mask [3] used to avoid parasitic inversion at the corners, as shown in FIG. 1.B. Commonly today and in this document, the term FinFET is used for both architectures. The DELTA and the FinFET are part of a group of transistors which can generally be referred to as multi-gate FETs (MG-FET) including double-gate (DG), triple and surrounding gate transistors [4]. These architectures have been developed to overcome the adverse effects that come along with CMOS scaling for higher switching speed and more densely integrated circuits according to Moore's law [5].

Some of the mentioned non-ideal effects have been identified as: (i) short-channel effects including voltage roll-off, (ii) drain-induced barrier lowering (DIBL), (iii) subthreshold slope degradation and (iv) non-negligible parasitic components [6]. Using a multi-gate architecture, a better control of the channel depletion is obtained with respect to a standard MOSFET and the influence of the drain electric field on the channel is reduced. Looking towards sensor CMOS integration, the scaling compatibility is an indispensable feature. Moreover, the advanced channel control provided by the FinFET architecture results in excellent sensor properties, as reported hereafter.

ISFET Principle:

Ion Sensitive Field Effect Transistors (ISFET) were first developed in the 1970s, as an alternative to the glass electrodes for pH and ion measurements. In comparison with a MOSFET (FIG. 2.A), the gate electrode is replaced by a reference electrode immersed in an aqueous solution in contact with the gate oxide, as illustrated in FIG. 2.B.

The voltage at the silicon surface is then function of the reference electrode and the amount of charges present in the solution as long as their contribution is not negligible at the ISFET surface. With respect to the voltage gate $V_g$ of standard MOSFET, additional contributions should then be considered [7]:

$$V_g = E_{ref} - \Psi + \chi_{sol} - \frac{\Phi_{Si}}{q} - \frac{Q_D}{C_{ox}} + \phi_S \qquad \text{Eq. 1}$$

Where $E_{ref}$ is the potential of the reference electrode, $\Psi$ is the chemical potential at the solution-oxide interface, $\chi_{sol}$ is the surface dipole potential of the solvent (usually constant), $\Phi_{Si}$ is the work function of the silicon which has been separated from the usual $\Phi_M$ of the metal gate now included in $E_{ref}$ and $\phi_S$ is the surface potential at the Si-Oxide interface which determines the $I_d(V_g)$ transfer characteristics.

$\Psi$ and $\phi_S$ are both surface potentials but they refer to two different interfaces in series. Any chemical variation of the solution modifies $\Psi$, which in case of pH can be expressed as $\Psi$(pH), but it can depend on any other electrical charges related to other ions or biological entities (DNA, proteins). The contribution of $\Psi$ is then linearly added to $\phi_S$, meaning that the electronic properties of the FET expressed by the $I_d$ ($V_{ref}$)) are not modulated by $\Psi$ but only shifted by a $\Delta\Psi$. A change in $\Psi$ will result in a change in the ISFET threshold voltage $V_{th}$, which can be measured by sweeping the reference electrode or by monitoring the $I_d$ value at fixed $V_{ref}$ value.

Previous Works Related to SiNWs for Sensing Applications

A list of references related to SiNWs for sensing applications is here reported. Information on the technology implemented in each work is mentioned as follows:

Technology Approach:
  Top-Down (TD): it consists in removing material from an initial substrate (e.g. silicon wafer) until structures are created;
  Bottom-Up (BU): small items (e.g. atoms or molecules) are assembled to create a larger device.

Silicon Substrate:
  Bulk: single-crystal piece cut and polished from larger single-crystal ingots;
  SOI: it consists of two silicon pieces separated by an insulator layer (usually SiO$_2$).

Architecture:
  FinFET: $H_{Fin}/T_{Fin}$ at least >1;
  Ribbon FET: $W_{Ribbon}/T_{Ribbon}$>1, including trapezoidal and triangular shape where $W_{bottom}$>$T_{Ribbon}$;
  ISFET: standard bulk MOSFET;
  Trigate FET with: $W_{Fin}/T_{Fin}\approx1$;
  GAA: Gate-All-Around, circular wire.

References Related to SiNWs for Sensing Applications:
  This invention: TD, Bulk, FinFET
  Microsens SA [8] TD, Bulk, ISFET
    Based on a standard MOSFET structure
  Abe et al. [9] TD, Bulk, ISFET
    Based on a standard MOSFET structure
  Lee et al. [10] TD, SOI, Ribbon FET
  Park et al. [11] TD, SOI, Ribbon FET
  Yoo et al. [12] TD, SOI, Ribbon FET
  Kim et al. [13] TD, SOI, Trigate FET
  Ahn et al. [14] TD, SOI, Trigate FET
  Ahn et el. [15] TD, Bulk, top side of a vertical FET
    see comment below
  Vu et al. [16] TD, SOI, Ribbon FET
  Cui et al. [17] TD, SOL GAA Tarasov et al. [18] TD, SOI, Ribbon FET
Chen et al. [19] TD, SOI, Ribbon FET
Zhang et al. [20] TD, SOI, Trigate FET
Li et al. [21] TD, SOI, Trigate FET
Hahm et al. [22] BU, SOI, GAA
Stern et al. [23] TD, SOI, Ribbon FET
Zheng et al. [24] TD, SOI,
Kim et al. [25] TD, SOI, Ribbon FET
Li et al. [26] BU, SOI, GAA
Wang et al. [27] BU, SOI, GAA
Zhang et al. [28] TD, SOI, Ribbon FET
Chiang et al. [29] TD, SOI, Ribbon FET
Patolsky et al. [30] BU, SOI, GAA Most of the available references are based on Ribbon-like structures. Some are based on GAA SiNWs fabricated by a bottom-up approach, which are not CMOS compatible. In [15] the exploited sensing surface is only the top side of the vertical FET while the body is embedded and controlled by lateral gates which are used for amplification purposes. Only one planar side of the device is involved in the detection mechanism limiting the potential advantages of a multi-gate vertical architecture. Contrarily in this invention, as presented in the following sections, the double-gate structure is fully immersed in the solution and the channel potential is controlled exclusively by the surrounding environment.

III. GENERAL EXPLANATION OF THE INVENTION

The innovation consists in the implementation of a well-defined electronic unit, namely a fully depleted FinFET fully immersed in a sensing environment (liquid, gas, solid). In nanoelectronics, the distinguish characteristics of a FinFET (FIG. 1.A) are its vertical architecture and conduction channels, generated by a metal gate (100), which completely surround a thin silicon "fin" (102). Its vertical architecture and multiple gate control provide higher stability and higher signal-to-noise ratio with respect to its planar counterpart, the ISFET, and common SiNWs. Moreover, such an architecture works under low applied voltages and currents, taking into consideration the power constraints of the CMOS semiconductor industry. In this invention, we provide a fabrication method which aims at the creation of FinFET as ionic, chemical and biological sensors on Si-Bulk. According to such method, the quality of such FinFETs on Si-bulk is expected to be equivalent to the one of FinFETs fabricated on SOI (Silicon-On-Insulator).

The present invention thus concerns a fabrication method of producing a FinFET sensor device comprising the steps of: providing a bulk silicon substrate; etching the silicon substrate to produce at least one upwardly extending Fin structure externally protruding from a surface of the silicon substrate; depositing a spacer layer on the at least one Fin structure; anisotropically etching a section of the spacer layer to expose the underlying silicon; isotropic or anisotropically etching of the exposed silicon surrounding the at least one Fin structure; and carrying out oxidation of the silicon surrounding the at least one Fin structure to produce a Fin structure of silicon inside the at least one Fin structure.

The bulk silicon substrate solely comprises silicon. A stress reducing layer can be deposited on the at least one Fin structure before depositing a spacer layer on the at least one Fin structure. A source and drain electrode are also provided.

The invention also relates to a FinFET sensor device produced by the above mentioned method. In particular, a FinFET sensor device including:

at least one source region;
at least one channel region between the drain region and the source region;
a bulk silicon substrate;
at least one upwardly extending Fin structure externally protruding from a surface of the bulk silicon substrate, the least one Fin structure including the at least one channel region, the at least one drain region and the at least one source region;
wherein the at least one Fin structure comprises a Fin structure of silicon inside the at least one Fin structure, the Fin structure of silicon including substantially vertical or upwardly extending sidewalls and having a ratio of a bottom thickness to a top thickness of the Fin structure of silicon between 0.3:1 and 0.8:1. Preferably, the Fin structure of silicon includes substantially vertical sidewalls having a ratio of a bottom thickness to a top thickness of the Fin structure of silicon between 0.65:1 and 0.8:1 and more preferably, between 0.65:1 and 0.78:1.

The present invention also relates to a sensing apparatus including a FinFET sensor device as mentioned above as well as a liquid, gas or solid to be sensed.

The invention also relates to a method of producing a three dimensional stack of FinFET sensor devices comprising the steps of: providing a silicon substrate; etching the silicon substrate to produce at least one upwardly extending Fin structure externally protruding from a surface of the silicon substrate; alternatively depositing first and second layers on top of each other so as to enclose the at least one Fin structure; etching at least one aperture through the first and second layer stack to create an oxidation cavity; carrying out oxidation in the oxidation cavity to produce a plurality of stacked individual silicon regions; etching to remove the first and second layer stack to expose the individual silicon regions; and providing source and drain electrodes.

The invention also relates to a three dimensional stack of FinFET sensor devices produced by the above method and a sensing apparatus including the above mentioned three dimensional stack of FinFET sensor devices as well as a liquid, gas or solid to be sensed.

IV. DETAILED EXPLANATION OF THE INVENTION

The invention is described in greater detail below through examples illustrated by the following Figures:

FIG. 1.A illustrates the DELTA transistor with metal gate, as it was originally proposed.

FIG. 1.B illustrates a cross-section of a FinFET.

FIG. 2.A illustrates a cross-section of a Metal-Oxide-Semiconductor (MOS) FET. FIG. 2.B illustrates a cross-section of a Ion Sensitive (IS) FET FIG. 3.A illustrates a cross-section of the starting Silicon substrate (300) for the fabrication process of FinFET sensors.

FIG. 3.B illustrates a cross-section of a stack of layers: $SiO_2$ (302), $Si_3N_4$ (304) and hydrogen silsequioxane resist (HSQ) (306), for the fabrication process of FinFET sensors.

FIG. 3.C illustrates a cross-section of the fabrication substrate after the FinFET e-beam lithography and its development (306).

FIG. 3.D illustrates a cross-section of the fabrication substrate after the FinFET anisotropic Deep Reactive Ion Etching (DRIE) of $Si_3N_4$ (304) and $SiO_2$ (302).

FIG. 3.E illustrates a cross-section of the fabrication substrate after the FinFET anisotropic Reactive Ion Etching (RIE) of Si (300).

FIG. 3.F illustrates a cross-section of the fabrication substrate after the isotropic Low Pressure Chemical Vapor Deposition of $Si_3N_4$ (308) and dry oxidation of $SiO_2$ (310).

FIG. 3.G illustrates a cross-section of the fabrication substrate after the FinFET anisotropic DRIE of $Si_3N_4$ reaching the Si bottom (312).

FIG. 3.H illustrates a cross-section of the fabrication substrate after the anisotropic RIE of Si, creating regions, of depth $D_e$, exposed to the oxidation (314).

FIG. 3.I illustrates a cross-section of the fabrication substrate after isotropic RIE of Si (318), as better alternative to the anisotropic etching.

FIG. 3.J illustrates a cross-section of the fabrication substrate after the FinFET wet oxidation (316) that detaches and clearly defines the FinFET sensors (320) from the Si substrate.

FIG. 3.K illustrates a cross-section of the source and drain pad (322) during implantation in presence of a photoresist mask (324).

FIG. 3.l illustrates a cross-section of the fabrication substrate after $Si_3N_4$ and $SiO_2$ isotropic etching reaching the FinFET bottom (326) and after Atomic Layer Deposition (ALD) of an insulator (328).

FIG. 3.M illustrates a cross-section of the source and drain pad (322) after the creation of the vias (329) through the insulator (328) and after the metallization for contacts (330).

FIG. 3.N is a SEM top view of a FinFET detail (a) and wire cross-sections by FIB after the $SiO_2$ etching: the Si vertical fin features $W_F$, =30 nm, $H_F$, =85 nm (b) and $W_F$, =20 nm, $H_F$, =65 nm (c).

FIG. 3.O is an optical image of the FinFET sensors with independent outputs and SU-8 openings over the sensing channels (left) and a SEM detail of a three SiNW FinFET (right).

FIG. 3.P shows the die-chip carrier assembly with FinFET sensors and transistors where a PDMS cube is patterned with microchannels at its bottom (left), and the sensing platform with PDMS embedding and Ag/AgCl reference electrode (right).

FIG. 4 illustrates the FinFET sensor with all its components: Si substrate (400), local $SiO_2$ insulation (402), dielectric (404), source (406), fin body (408), drain (410), a sensing environment, e.g liquid (412), an external reference electrode (414) and an integrated reference electrode.

FIG. 5.A illustrates a cross-section of the fabrication substrate for 3D stack of FinFETs after e-beam lithography, DRIE and RIE of the Si substrate corresponding to the fabrication step for single FinFET of FIG. 3.E with the difference that a deeper etching into the Si-bulk is performed.

FIG. 5.B illustrates a cross-section of the fabrication substrate for 3D stack of FinFETs after repeated deposition of $SiO_2$ (Low Temperature Oxide, LTO) (502) and LPCVD $Si_3N_4$ (504).

FIG. 5.C illustrates a cross-section of the fabrication substrate for 3D stack of FinFETs after DRIE that creates apertures (506) in the stack of layers $SiO_2$—$Si_3N_4$ previously deposited.

FIG. 5.D illustrates a cross-section of the fabrication substrate for 3D stack of FinFETs after wet/dry oxidation: the water vapor or oxygen diffuse through the $SiO_2$ layers and oxidize the Si (508) separating the different FinFETs between each other (500 and 501) and from the bottom (510).

FIG. 5.E illustrates a cross-section of the fabrication substrate for 3D stack of FinFETs at the end of the process: a $SiO_2$ wet etching allows to release and suspend all the FinFET matrix (512) over the Si bottom (510) and the insulating bottom layer (508).

FIG. 5.F illustrates a cross-section of the fabrication substrate for 3D stack of FinFETs in three dimension at the end of the process: a $SiO_2$ wet etching allows to release and suspend all the FinFET matrix (512) over the Si bottom (510) and the insulating bottom layer (508).

Figure 6:
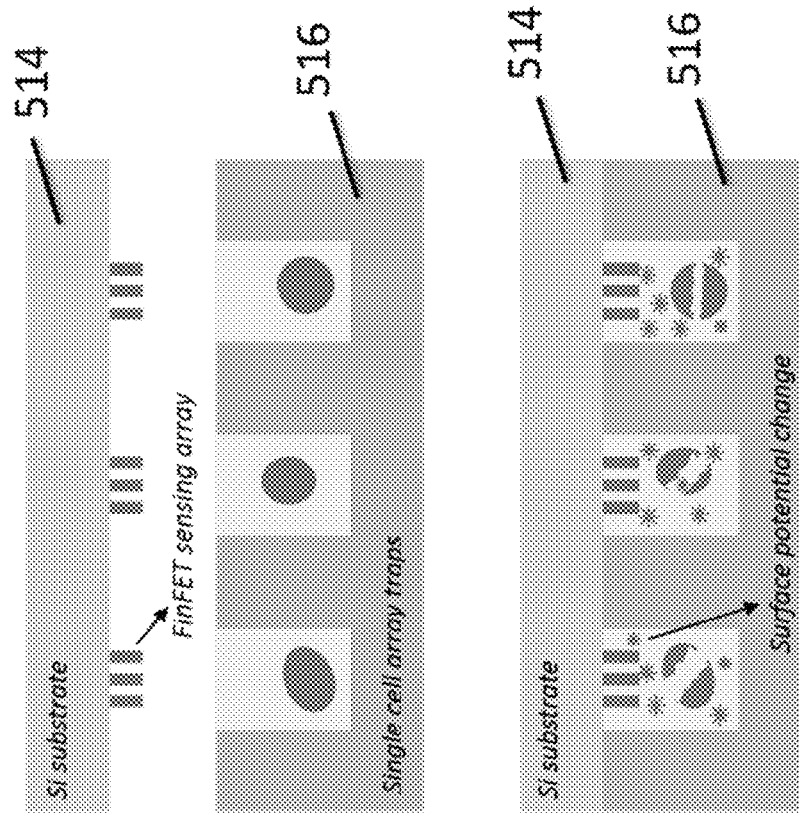

FIG. 6 illustrates a cross-section of a single-cell trapping array (516) with FinFET sensors integrated in the top cover (514).

FIG. 7.A illustrates a FinFET cross-section with fully exposed surface: the fin body (600) with two lateral vertical sidewalls (604), a top side (606) and a dielectric (602) surrounding the fin body.

FIG. 7.B illustrates a Tri-gate FET cross-section with fully exposed surface: the fin body (600) with two lateral vertical sidewalls (606), a top side (608) and a dielectric (602) surrounding the fin body.

FIG. 7.C illustrates a DGFET cross-section with fully exposed surface: the fin body (600) with two lateral vertical sidewalls (610) and a dielectric (602) surrounding the fin body.

FIG. 7.D illustrates a FinFET cross-section with partially exposed surface: the fin body (600) with two lateral metal gates (612), a top exposed side (613) and a dielectric (602) surrounding the fin body.

FIG. 7.E illustrates a FinFET cross-section with partially exposed surface: the fin body (600) with two lateral metal gates (612), a top exposed FinFET (614) and a dielectric (602) surrounding the fin body.

Figure 8:
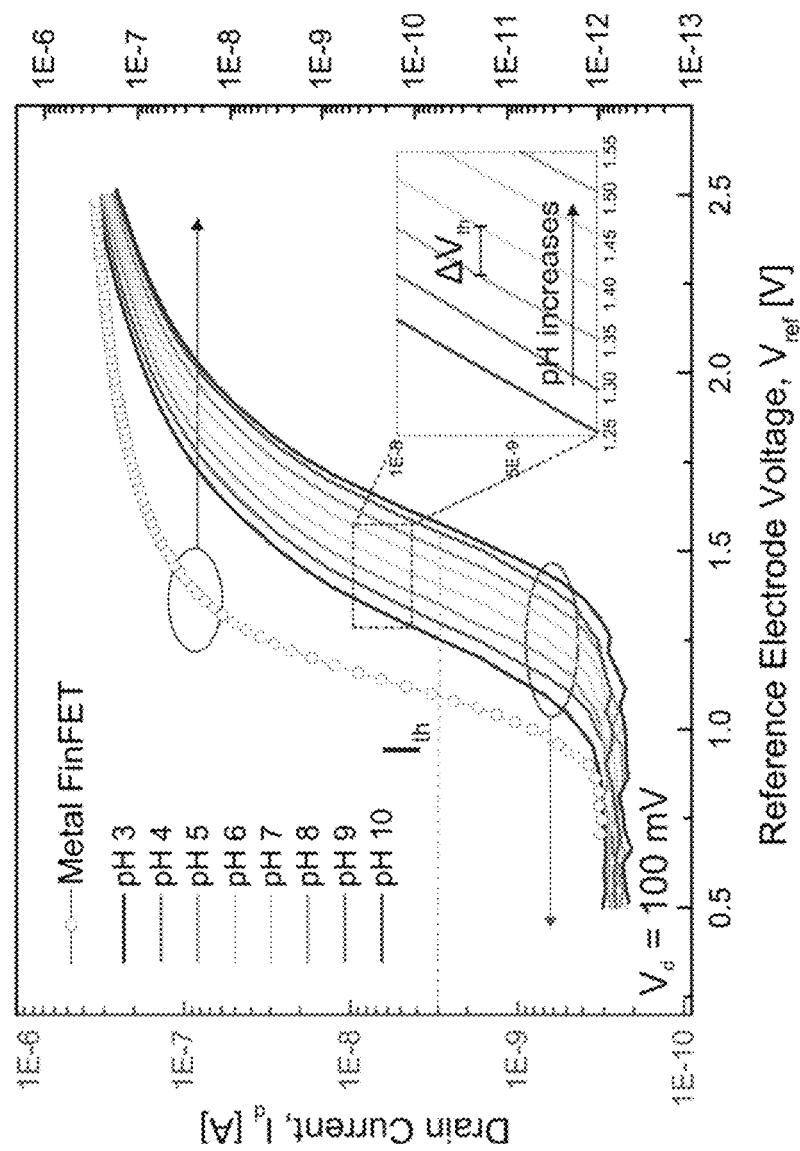

FIG. 8: $I_d(V_{ref})$ characteristics for a metal (right Y-axis) and liquid gate (left Y-axis) FinFET sensor at $V_d$=100 mV, $V_b$=0 V. The FinFET sensor characteristics have been obtained for 3≤pH≤9 with the inset showing the curve shift $\Delta V_{th}$/pH due to the surface potential variation at different pH values.

Figure 9:
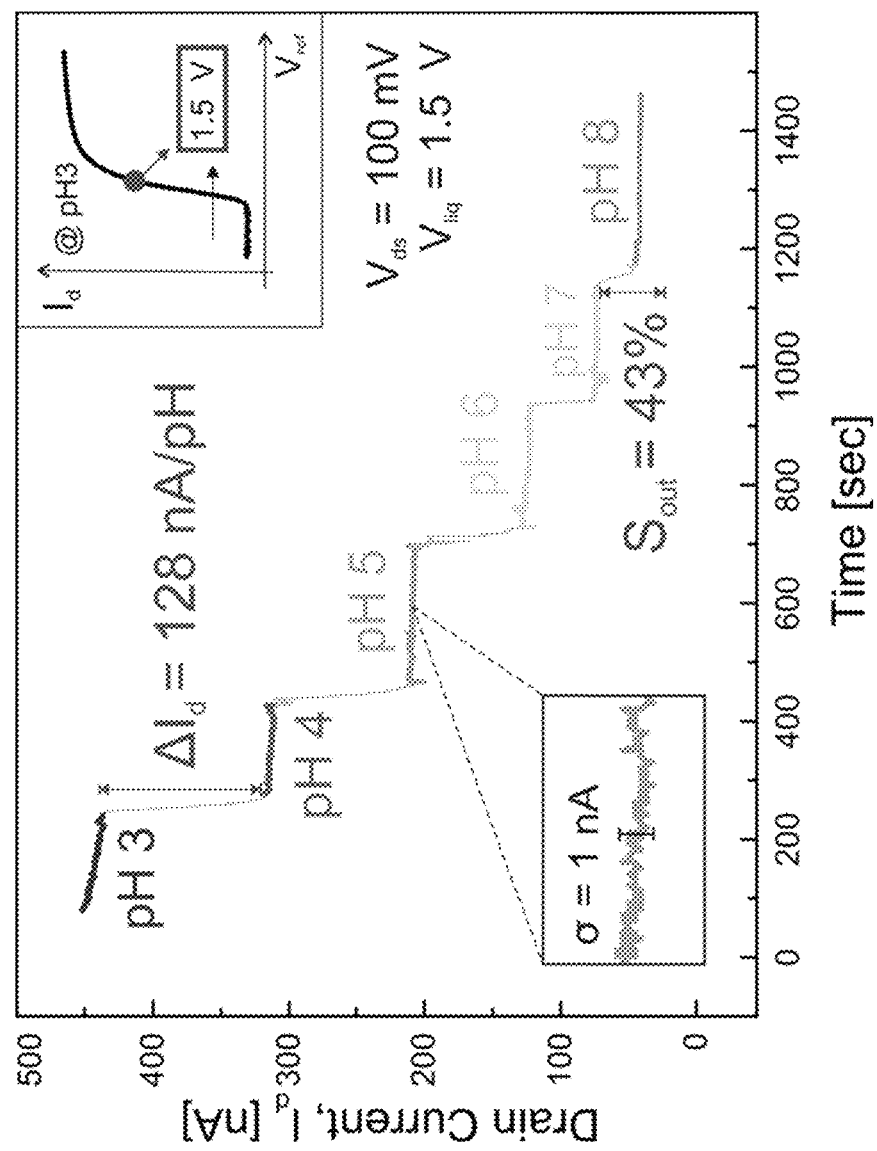

FIG. 9: Measured Drain Current $I_d$, for a FinFET sensor during a time period of 25 minutes for 3≤pH≤9 with reference electrode $V_{ref}$=1.5 V and $V_{ds}$=100 mV.

Figure 10:
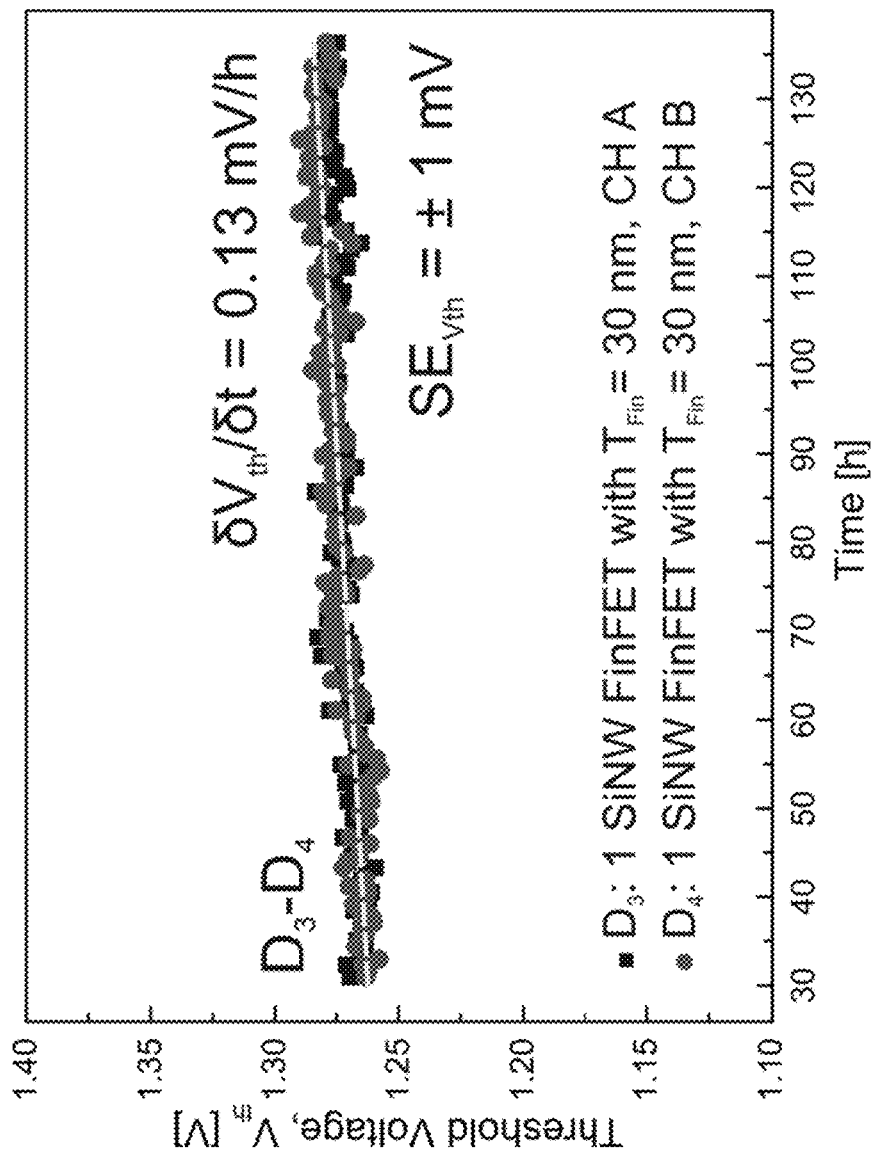

FIG. 10: Long-term stability measurement over 4.5 days; the threshold voltage $V_{th}$ is monitored for different FinFET sensors at constant pH=6.

Figure 11:
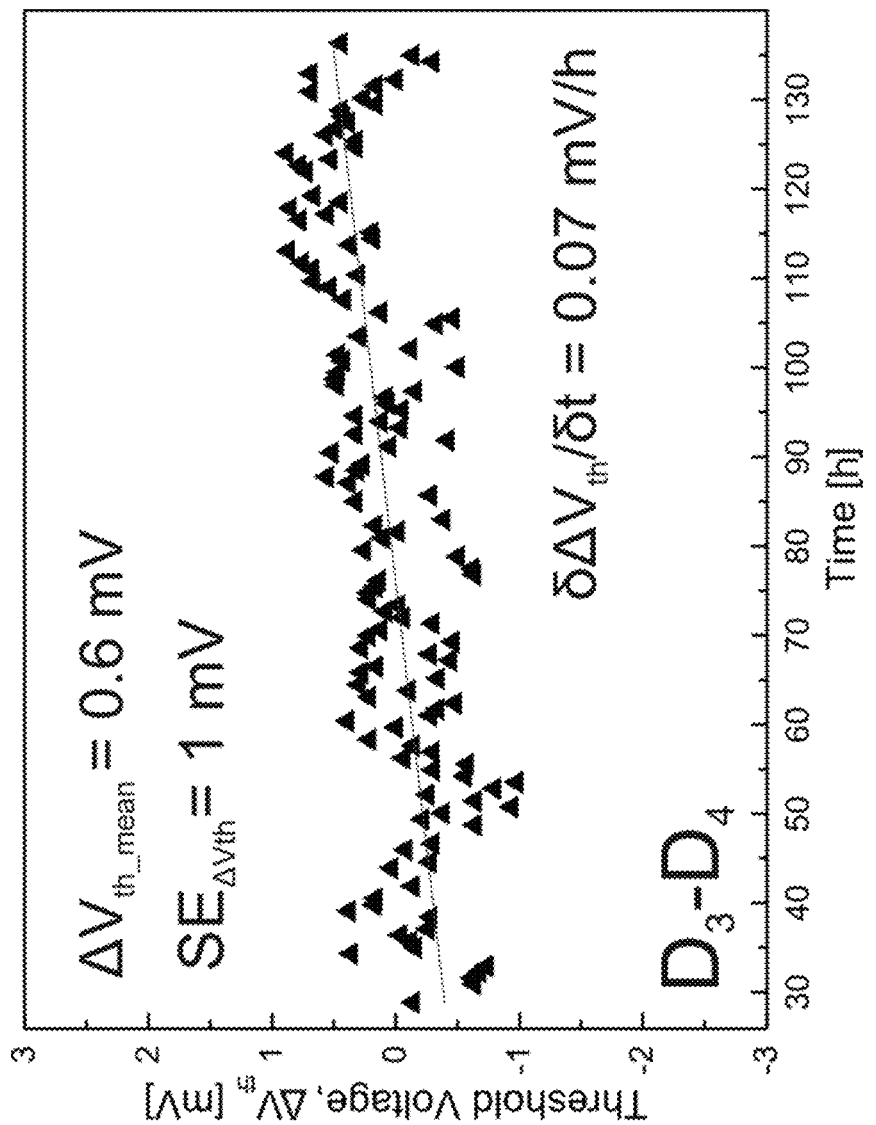

FIG. 11: Result of the subtraction of the date set of $V_{th}$ for two identical FinFETs located at two different positions on the same die.

Figure 12:
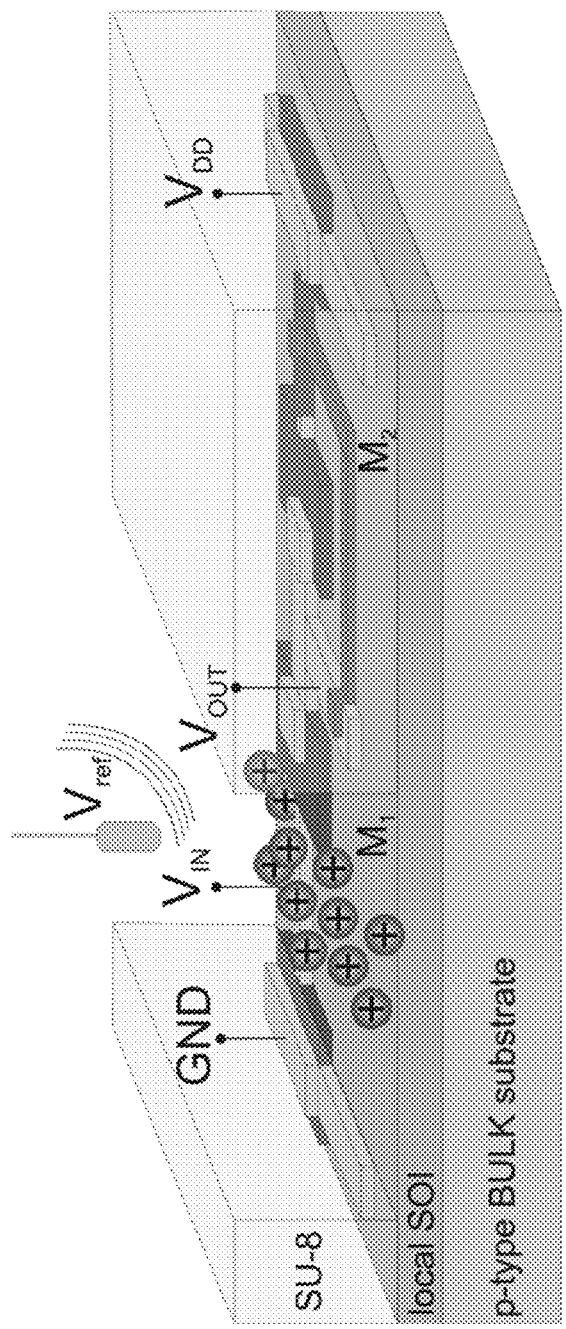

FIG. 12: Schematic representation of the proposed pH sensor with a sensing FinFET exposed to the $H^+$ solution and reference electrode (left), connected to a metal gate FinFET protected by an SU-8 layer (right).

Figure 13:
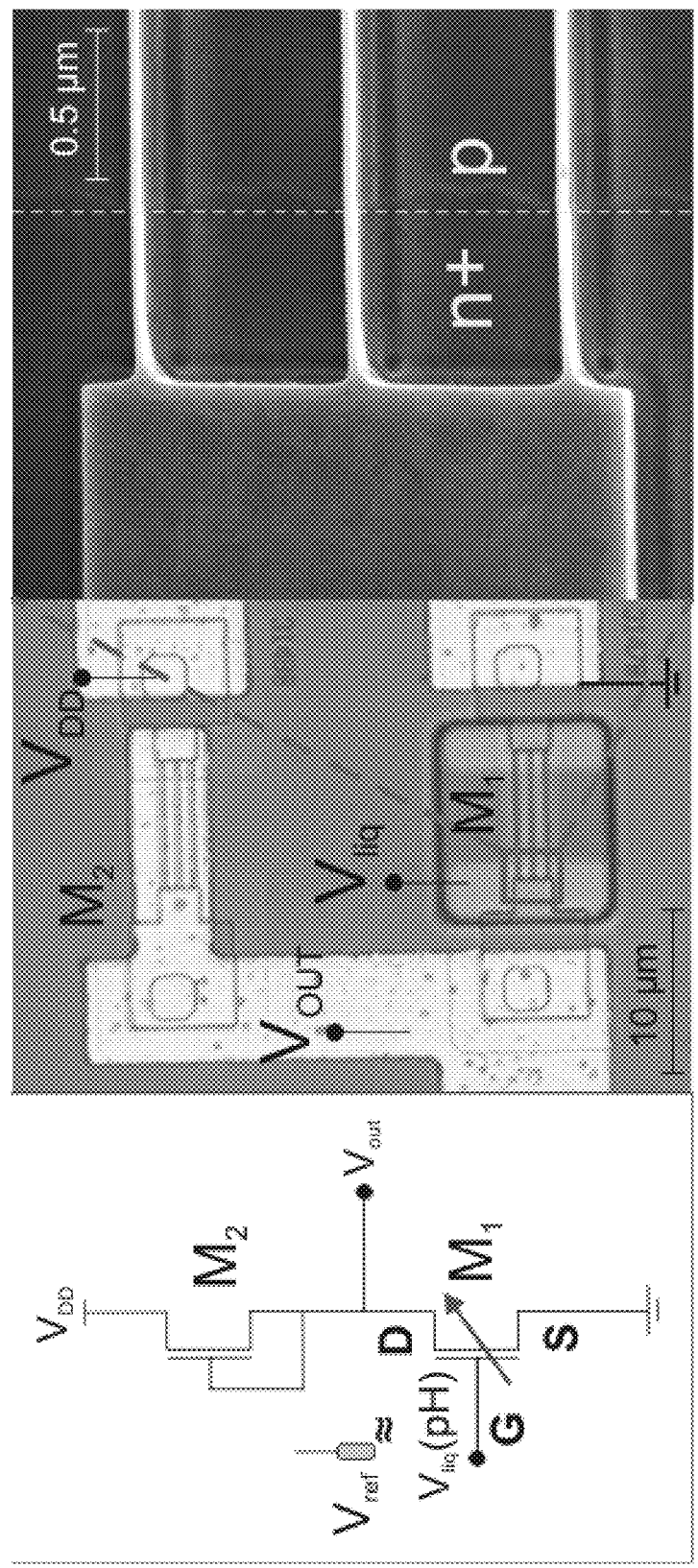

FIG. 13: Schematic representation of the proposed pH sensor with a sensing FinFET exposed to the $H^+$ solution and reference electrode (left), connected to a metal gate FinFET protected by an SU-8 layer (right).

Figure 14:
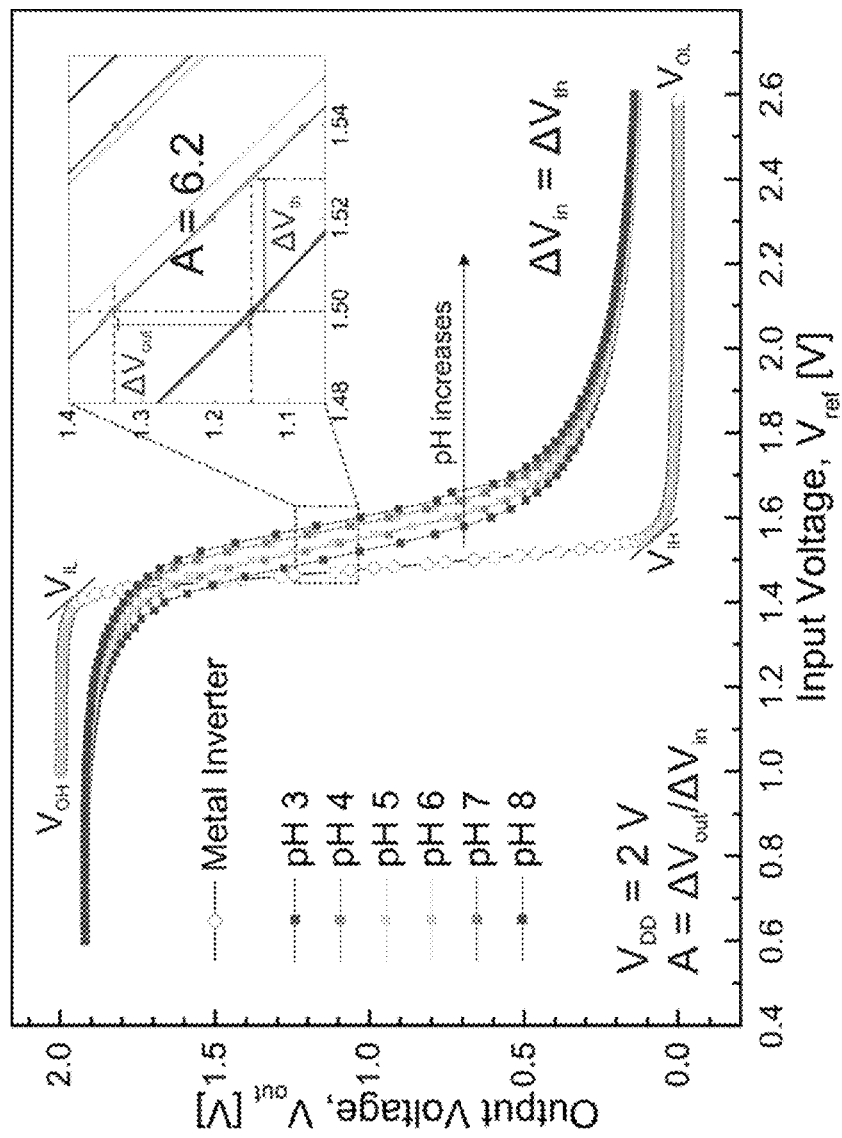

FIG. 14: $V_{out}(V_{ref})$ characteristics of the metal gate (black curve) and sensing (colored curves) FinFET amplifier described in FIG. 3, at $V_{DD}$=2 V, for fins with $H_{Fin}$=100 nm, $L_{Fin}$=10 μM, $T_{FinM1}$=30 nm and $T_{FinM2}$=40 nm. The FinFET-based sensing amplifier $V_{out}(V_{ref})$ has been measured for 3≤pH≤8; the inset shows the curve shift $\Delta V_{pH}$ along with the corresponding $\Delta V_{out}$.

FIG. 15.A: Simulated fin cross-section, showing the improvement obtained by an isotropic etching with respect to an anisotropic etching.

FIG. 15.B: Fin cross-section obtained by isotropic Si substrate etching, corresponding to simulated structure in FIG. 15.A (4).

Figure 16:
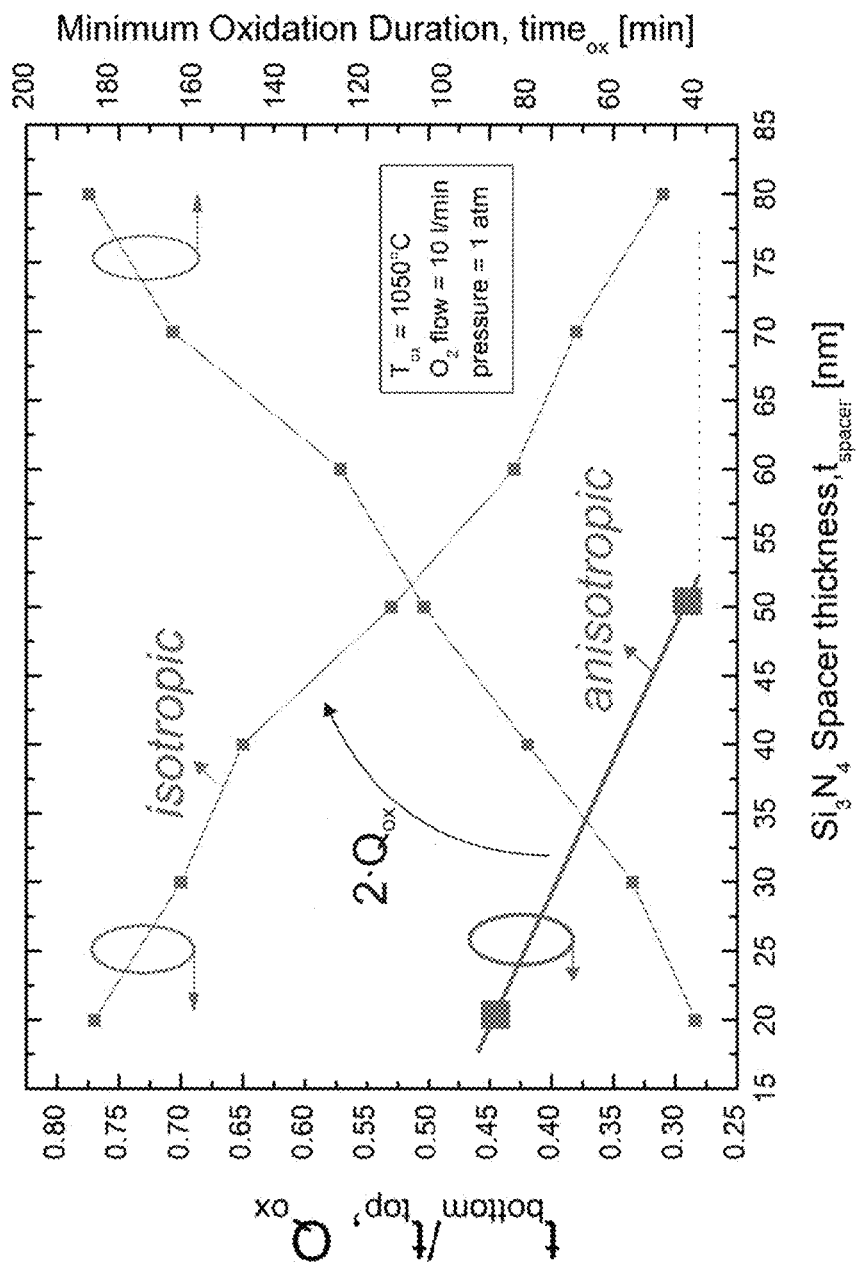

FIG. 16 illustrates the variation of the quality factor $Q_{ox}$ according to the spacer thickness 328 and the type of etching of the Si substrate (314 or 318) for an oxidation temperature of $T_{ox}=1050°$ C., oxygen flow 10 l/min and furnace chamber pressure of 1 atm.

Method to Fabricate Finfet Sensors On Si-Bulk

The FinFETs were fabricated using a local Si-bulk oxidation technology on boron doped Si-bulk wafers. Fin widths from 15 to 40 nm and $H_{Fin}/W_{Fin}>3$ have been achieved. Source and drain contacts were implanted with a Phosphorous dose $\approx 10^{16}/cm^2$ at 30 keV, aimed at reaching a contact doping level $N_a=10^{20}$-$10^{21}/cm^3$ and expected penetration depth of 150 nm. The fin surface was covered by 8 nm of $HfO_2$ deposited by ALD (Atomic Layer Deposition). In order to prevent any surface degradation the use of highly concentrated HF acid (Hydrofluoric) solution and high power $O_2$-plasma was avoided after ALD. The metal connections were fabricated by a lift-off process of AlSi with 1% Silicon to avoid Al diffusion at the junctions. SU-8 is used to prevent the contact between the liquid and the metal. SU-8 is a negative photoresist which is chemically very inert and thermally stable. SU-8 openings were patterned next to the sensor channels, as shown in FIG. 3.O (left). The correct superposition of the liquid opening and doped regions (FIG. 3.O, right) allow the n-channel to conduct when the solution is biased at the proper potential. Liquid and metal gate FinFETs are both available on the same die, as represented in FIG. 3.P (left). Once the die was diced from the wafer, it was connected to the chip carrier by ball-bonding with Au wires. For the assembly of the microfluidic platform, PDMS microchannels were aligned with respect to the SU-8 openings and Epoxy fixed them at chip carrier. The channels were then connected by PTFE tubes and a full PDMS embedding seals the whole system (FIG. 3.P, right).

Exemplary Process for Producing FinFETs:

a) Substrate: The starting substrate is a p-type Silicon wafer 300 (FIG. 3.A), for example, single side polished, with a resistivity of 0.1-0.5 Ohm·cm, a diameter of 100 mm and thickness of 525 m. No insulated layer (SOI, Silicon-On-Insulator) is available on the substrate. The resistivity and doping value can change according to the wanted electric characteristics.

b) Substrate preparation: Three layers are deposited in series (FIG. 3.B):
  1. 0.1-10 nm thick $SiO_2$ (302) deposited by dry-wet oxidation. The function of this layer is to drastically reduce the stress induced by $Si_3N_4$, especially for very long sensors. Too high induced stress causes the formation of wreckage point after bulk oxidation described at point f)
  2. 0.1-150 nm thick $Si_3N_4$ (304) deposited by LPCVD or MOCVD as hard mask
  3. 0.1-150 nm thick hydrogen silsequioxane resist (HSQ) (306)

All thicknesses are intended as optimized and may vary from the mentioned ones.

c) Fin thickness $T_{Fin}$ definition: The fin thickness, the source and drain pads are defined by Electron Beam Lithography (FIG. 3.C). The EBL step is realized by exposure of the hydrogen silsequioxane resist (HSQ) (306), previously deposited.

d) Nitride etching: The patterned HSQ is transferred into the $Si_3N_4$ mask by $SF_6$ based Deep Reactive Ion Etching (FIG. 3.D). Using $SF_6$ as chemical base it is possible to obtain a recipe with high selectivity with respect to HSQ which at high exposure dose is chemically similar to $SiO_2$. This way the HSQ mask can be completely transferred into the $Si_3N_4$ hard mask preserving a very high definition of the top fin thickness. To obtain such selectivity the power supplied to the chuck should not exceed 10 W. Alternative chemistry and chuck power may be considered.

e) Fin height definition: The $Si_3N_4$ hard mask is transferred into the Silicon substrate by $Cl_2$ based RIE (FIG. 3.E). The optimal fin (vertical or extending upwardly) height is (about) 200 nm.

f) $Si_3N_4$ spacer creation: By Low Pressure Chemical Vapor Deposition (LPCVD) 50 nm of $Si_3N_4$ (FIG. 3.F) (308) are deposited and etched to form the so-called $Si_3N_4$ spacers. In order to reduce the $Si_3N_4$ stress on the Si fin, 5 nm of $SiO_2$ (310) can also be deposited before the nitride. In this optimized method the spacer thickness is between 20-30 nm, which guarantees the best vertical output for the fins. The mentioned $SiO_2$ interfacial layer is limited between 0.1-5 nm.

g) $Si_3N_4$ spacer etching: The nitride is anisotropically removed from the bottom (312), as shown in (FIG. 3.G). The isotropic deposition and the previous remaining $Si_3N_4$ mask on top of the fins allow a homogeneous encapsulation around the fin. The previous described $Si_3N_4$ etching recipe based on $SF_6$, described at point c), is not suitable for this particular etching:
  1. The spacer etching needs to be anisotropic in order not to consume the nitride on the fin sidewalls. On the contrary, the recipe based on $SF_6$ is quite isotropic, especially because of the low chuck power;
  2. The etch rate should be slower in order to be more accurate on the etching time and avoid an over-etching which would reduce the spacer thickness;
  3. The etching time should include a small over-etching time, otherwise, if any $Si_3N_4$ remains, the oxidation would not take place. At the same time, the recipe should stop with a certain selectivity at the Si bottom, which is etched too fast by $SF_6$.

For these reasons $CF_4$ at chuck power around 40 W represents an optimized choice with respect to $SF_6$.

h) Si substrate exposure: An additional RIE Si etching (FIG. 3.H) is needed to guarantee the formation of well-defined vertical fin. In the proposed invention:
  1. The optimal etching depth, $D_e$ (314), is higher than 50 nm to assure optimal vertical structure after the oxidation. For $D_e<50$ nm the fin are not symmetric with respect to a central vertical axis (unbalanced mechanical force of the oxidation). This method guarantees the minimum space for the oxidation in order not to affect their position and shape.
  2. The optimal etching depth, $D_e$, is lower than 200 nm. For $D_e>200$ nm, the oxidation may not produce enough $SiO_2$ (FIG. 3.I)(316) for a full FinFET insulation.
  3. The best condition for such etching has been determined to be isotropic (318) instead of anisotropic, as illustrated (FIG. 3.J and FIG. 15.A). This condition allows to drastically improve the quality of the vertical sidewalls, as it is possible to observe in the simulated fin cross-section. The quality of the resulting structures is defined by the factor $Q_{ox}$, an index of quality of the vertical sidewalls equal to the ratio $T_{bot}/T_{top}$ where $T_{top}$ is the top Fin thickness as defined by EBL, and $T_{bot}$ is the fin thickness measured at a predetermined distance of, for example, $H_{Fin}=150$ nm from $T_{top}$, in the case illustrated in the Fin structure 320 in FIG. 3.J (middle Fin structure) and FIG. 15.A. The goal is to be able to reproduce the quality of SOI equivalent structures which would have a $Q_{ox}=1$. The quality factors is then in the range $0<Q_{ox}<1$. In FIG. 15.A, it is shown how the isotropic etching allows to improve $Q_{ox}$ from 0.45 to 0.78 in Finite Element Analysis. In FIG. 15.B the simulated structure is fabricated with a resulting $Q_{ox}=0.8$. The factor $Q_{ox}$ also depends on other type of variables, such as the spacer thickness 308 and the oxidation duration. FIG. 16 illustrates how $Q_{ox}$ varies according to those variables. For the isotropic etching, $Q_{ox}$ is in the range 0.3 to 0.78 ($H_{Fin}=150$ nm from $T_{top}$) while for the anisotropic etching $Q_{ox}$ is in the range 0.25 to 0.45. Fixing all variables, the improvement from one etching to another is expected to be close to 1.8.

i) LOCAL Si-Bulk oxidation: 300 nm of $SiO_2$ (316) are grown by wet or dry oxidation, detaching and isolating the vertical fins (320) from the bulk (FIG. 3.J). Such local oxidation, allow to achieve fin thickness, $T_{Fin}$, ranging from 15 to 40 nm and $H_{Fin}/T_{Fin}=3$, as also shown in FIG. 3.N. FIG. 15.B shown the fin cross-section when the Si substrate exposure is realized by isotropic etching, obtaining an excellent quality factor, $Q_{ox}=0.8$.

j) Source and drain implantation: The $Si_3N_4$ spacers are then removed by hot phosphoric acid. Source and drain pads (322) are implanted with phosphorous at 25 keV with $n_A=10^{15}$ cm$^{-3}$ as dose (FIG. 3.K), creating n-channel device with n+ contacts. Photoresist (324) is an optimal implantation mask, since its removal does not affect the surface of the sensing channel. Any other material, such as $SiO_2$ or $Si_3N_4$, are possible but they imply a removal etching step affecting the sensing surface.

k) Gate oxide: The fin surface is then exposed by Dip Hydrofluoric (HF) acid (FIGS. 3.L and 3.N) to guarantee the fin to be maximally exposed but preventing the $SiO_2$ etching under the fin (326). The use of the FinFET as sensor in a liquid and dry environment should take into account stiction problems due to water force. As alternative, the structures can be fully cleared from the $SiO_2$ and immersed in a liquid environment. The whole wafer is then covered by 8 nm of $HfO_2$ deposited by Atomic Layer Deposition (328).

l) Contacts: Vias of 3×3 μm² are created by Ar ion milling (329) through the gate oxide (328), and the devices are connected with $AlSi_{1\%}$ lines (330) to 250×250 μm² pads at the edge of each die (FIGS. 3.M and 3.O). For FinFETs aimed at the electrical characterization an AlSi1 % metal gate (331) is also deposited (FIG. 3.P). Chemical Mechanical Polishing (CMP) and a backside metallization are performed for a good chuck contact.

m) Liquid isolation: SU-8 openings (332) were patterned next to the FET sensing channels to prevent the contact between liquid and the metal connections (FIG. 3.O).

n) Packaging: The wafer was diced, each die is glued into the chip carrier and connected by Au wires (334) (FIG. 3.P)

FIG. 4 includes all the FinFET sensor components described by the fabrication method here above:

[400] Bulk substrate
[402] Local Si-Bulk insulation ($SiO_2$) obtained with the fabrication method described above
[404] Dielectric
[406] Source
[408] Fin body
[410] Drain
[412] Fully immersing sensing environment
[414] External reference electrode
[416] Integrated reference electrode In order to operate as sensor, the FinFET is fully immersed in a liquid (gas or solid) environment (FIG. 3.P) whose potential is controlled by an external (336) or integrated reference electrode. The sensing environment can be controlled by an active pumping system where the flow is moved by a drop of pressure. The FinFET chip can be connected to such pumping system through polymer tubes (FIG. 3.P) (338). In alternative, passive microfluidic can also be conceived. Such passive system are based on different physics principles, such as temperature different or change in surface roughness.

Moreover, all contact potentials (reference electrode, source, drain and back gate) are controlled by a voltmeter connected to the FinFET sensor through a PCB (340) and directly to the reference electrode.

Exemplary Process for Producing 3D Stack of FinFETs:

In this embodiment, the fabrication method described above is implemented for 3D stack of FinFETs with the following modification:

a) (previous point e) Fin height definition: Si is etched more deeply into the bulk, according to the numbers of wanted fins and their height. As an example, two fins (500 and 501) can be targeted in the same monolithic fin structure, each with an approximate height of 200 nm (FIG. 5.A). For a total height of minimum 400 nm.

b) $Si_3N_4$—$SiO_2$ stack: layers of $SiO_2$ (502) and $Si_3N_4$ (504) are alternatively anisotropically deposited covering the whole fin height (FIG. 5.B). The height of 504 covers the fin height that should be protected from the oxidation (the final fin height) while the height of 502 depends of the wanted vertical distance between each fin. An optimal ratio between $SiO_2$ and $Si_3N_4$ is 1:2.

c) Oxidation apertures: vertical apertures (506) are created through the $Si_3N_4$—$SiO_2$ layer stack by Deep Reactive Ion Etching, reaching the bottom Si (FIG. 5.C).

d) Si oxidation: dry or wet oxidation is performed (FIG. 5.D). Thanks to cavities (506) created at previous point c) the water vapor or oxygen can reach the whole fin depth. The $Si_3N_4$ (504) does not allow the Si oxidation because of its impermeability, while the oxidation flux will diffuse trough the $SiO_2$ (502) and will oxidize the Si between the two fins (508) and at the Si bottom (510).

e) $Si_3N_4$—SiO2 etching: after oxidation the 3D stack includes the following layers:
(Two) separated fins (500 and 501)
$SiO_2$ (508) grown by oxidation which separates 500 and 501 and it also covers the Si bottom 510.
The sacrificial layers 502 and 504 deposited to achieve the selective oxidation
The Si substrate 510
Wet etching is used to remove all layers except the fins 500 and 501. Supposing that more fins have been created, the final result (FIG. 5.E and FIG. 5.F) is the array 512 of vertically stacked fins with height and separation distance defined respectively by 504 and 502. According to the etching time, an insulating layer of $SiO_2$ 508 can be left at the Si bottom 510.

Such an array is finally filled with a liquid (or other) sensing environment so that all the FinFET sensors will be biased by the same surface potential Ψ.

Single-Cell Chamber:

In this embodiment, the fabrication of single, multiple and 3D stack FinFETs (514) is combined with a micro-holed Polydimethylsiloxane (PDMS) array (516) for the confinement of single cells (FIG. 6). The PDMS support is simple patterned by standard or e-beam lithography. The FinFET sensor assume two functions in such embodiment:

FinFET first act as electrode for electrophoresis. Electrophoresis implies the control of the cell membrane upon biasing the solution with a RF signal. According to the frequency the cells are obliged to absorb water up to the fracture of the membrane. The cytosol is then mixed with the solution.

FinFET sensors are then capable to detect a specific cytosol concentration. According to their surface they can detect salt, ion or specific protein.

FinFET Sensor Configurations

All the following devices are to be intended as FinFET sensors, on Si-Bulk fabricated with the method described above. While the general FinFET sensor architecture is represented in FIG. 4, the device cross-sections may vary as follows:

1. FinFET with Fully-Exposed Surface (FIG. 7.A)

The FinFET is fully immersed in the surrounding medium which, together with species to be detected, generates a surface potential $\Psi$. The electrical outputs (transfer or output characteristics, current in time) of the device is function of the charged species in the environment. Supposing the sensing environment to be liquid, such potential can be expressed as $V_{liq}$.

The FinFET, as illustrated in FIG. 7.A, is defined by:
  $T_{Fin}$: Fin thickness on the x-axis
  $H_{Fin}$: Fin height on the y-axis
  $L_{Fin}$: Fin length on the z-axis
  $t_{ins}$: thickness of a surrounding insulator (also meant as native oxide)
  $\in_{ins}$: dielectric constant of a surrounding insulator (also meant as native oxide)

The following specifications apply:
  $H_{Fin} > T_{Fin}$
  Full liquid gate, surrounding the Si fin (600)
  Two lateral gates can at least be defined (604 and 606)
  Uniform potential ($V_{liq}$) generating a uniform surface potential ($\Psi$) on all FinFET sides (604 and 606)
  Undefined insulator, $HfO_2$ as example (602)

In this embodiment (FIG. 7.A) the surface is fully exploited for the sensing and the FinFET surface potential $\Psi$ is generated by a uniform surrounding environment. Conduction channels are generated on the lateral device sidewalls (604) and the top side (606). We considered that a FinFET is equivalent to the definition of Tri-gate FET device or a Double-Gate (DG) FET (see configuration B and C for differentiation)

2. Tri-Gate FET with Full-Exploited Surface (FIG. 7.B)

The Tri-gate FET is defined by:
  $T_{Fin}$: Fin thickness on the x-axis
  $H_{Fin}$: Fin height on the y-axis
  $L_{Fin}$: Fin length on the z-axis
  $t_{ins}$: thickness of a surrounding insulator (also intended as native oxide)
  $\in_{ins}$: dielectric constant of a surrounding insulator (also intended as native oxide)

The following specifications apply:
  $H_{Fin} > T_{Fin}$
  Full liquid gate, surrounding the Si fin (600)
  $T_{Fin}$ is not negligible
  Three lateral gates can be defined (606 and 608)
  Uniform potential ($V_{liq}$) generating a uniform surface potential ($\Psi$) on all FinFET sides (606 and 608)
  Undefined insulator, $HfO_2$ as example (602)

with $H_{Fin} > T_{Fin}$ and $T_{Fin}$ is not negligible. The definition of Tri-gate arises from the possibility of precisely defining three gates exposed to the sensing environment, as illustrated in FIG. 7.B. $T_{Fin}$ is considered not negligible when $T_{Fin} > 2\, H_{Fin}/x$, where x is a value equal or higher than 10.

In this embodiment (Fig. C) the surface is fully exploited for the sensing and the FinFET surface potential $\Psi$ is generated by a uniform surrounding environment. Conduction channels are generated on the lateral device sidewalls (606) and the top side (608).

3. Double-Gate (DG) FET with Full-Exploited Surface (FIG. 7.C)

The Double-Gate FET is defined by:
  $T_{Fin}$: Fin thickness on the x-axis
  $H_{Fin}$: Fin height on the y-axis
  $L_{Fin}$: Fin length on the z-axis
  $t_{ins}$: thickness of a surrounding insulator (also intended as native oxide)
  $\in_{ins}$: dielectric constant of a surrounding insulator (also intended as native oxide)

The following specifications apply:
  $H_{Fin} > T_{Fin}$
  Full liquid gate, surrounding the Si fin (600)
  $T_{Fin}$ is negligible
  Two lateral gates can be defined (610)
  Uniform potential ($V_{liq}$) generating a uniform surface potential ($\Psi$) on all FinFET sides (610)
  Undefined insulator, $HfO_2$ as example (602)

with $H_{Fin} > T_{Fin}$ and $T_{Fin}$ may be negligible. The definition of DGFET arises from the possibility of precisely defining two gates (610), exposed to the sensing environment, as illustrated in FIG. 7.C, and neglecting one gate which contributes less to the total transistor current. In this embodiment (FIG. 7.C) the surface is fully exploited for the sensing and the FinFET surface potential $\Psi$ is generated by a uniform surrounding environment. $T_{Fin}$ is considered negligible when $T_{Fin} \leq 2\, H_{Fin}/x$, where x is a value equal or higher than 10. Conduction channels are then generated only on the lateral device sidewalls (610).

4. FinFET with Lateral Gates of Maximum Height (FIG. 7.D)

In this embodiment (FIG. 7.D), the metal gate of a standard FinFET is partially replaced by a gating environment (liquid, gas or solid) containing species to be detected (pH, other chemical ions, biological entities). As illustrated in FIG. 7.D, the metal gates (612) cover the total Fin height and the only surface exploited for sensing is the top planar part (613). This hybrid device (planar+DGFET) is defined by:
  $T_{Fin}$: thickness on the x-axis
  $H_{Fin}$: height on the y-axis
  $L_{Fin}$: length on the z-axis
  $t_{ins}$: thickness of a surrounding insulator (also intended as native oxide)
  $\in_{ins}$: dielectric constant of a surrounding insulator (also intended as native oxide)
  $H_{Gate}$: gate height on the y-axis The following conditions apply:
  $H_{Fin} > T_{Fin}$
  Two lateral gates can at least be defined
  Metal gates are present (612), covering the whole fin height, $H_{gate} = H_{Fin}$ Two different potentials are applied ($V_{liq}$ and $V_g$) generating a non-uniform surface potential ($\Psi$) on the fin body (600).

Undefined insulator, HfO$_2$ as example (602)

In this embodiment, $H_{Gate}=H_{Fin}$. Supposing the sensing environment to be liquid, such potential can be expressed as $V_{liq}$. The potential applied through the metal gate is called $V_g$. Only the top surface is exploited for the sensing and the device surface potential $\Psi$ is generated by two different applied potential: $V_g$ and $V_{liq}$. Conduction channels are generated in correspondence to the lateral metal gates (612) and the sensing surface (613).

5. FinFET with Lateral Gates of Maximum Height (FIG. 7.E)

In this embodiment (FIG. 7.E), the metal gate of a standard FinFET is partially replaced by a gating environment (liquid, gas or solid) containing species to be detected (pH, other chemical ions, biological entities). As illustrated in FIG. 7.E, the metal gates (612) do not cover the total Fin height. Only the top part (614) is exploited as sensor. This hybrid device (FinFET+DG-FET) is defined by:

$T_{Fin}$: thickness on the x-axis
$H_{Fin}$: height on the y-axis
$L_{Fin}$: length on the z-axis
$t_{ins}$: thickness of a surrounding insulator (also intended as native oxide)
$\in_{ins}$: dielectric constant of a surrounding insulator (also intended as native oxide)
$H_{Gate}$: gate height on the y-axis The following conditions apply:
$H_{Fin}>T_{Fin}$
Two lateral gates can at least be defined
Metal gates are present (612), but $H_{gate}<H_{Fin}$
Two different potential are applied ($V_{liq}$ and $V_g$) generating a non-uniform surface potential ($\Psi$) on the fin body (600).
Undefined insulator, HfO$_2$ as example (602)

In this embodiment, $H_{Gate}<H_{Fin}$. Supposing the sensing environment to be liquid, such potential can be expressed as $V_{liq}$. The potential applied through the metal gate is called $V_g$. Only the top surface is exploited for the sensing and the device surface potential $\Psi$ is generated by two different applied potential: $V_g$ and $V_{liq}$. Conduction channels are generated in correspondence to the lateral metal gates (612) and the sensing surface (614).

Main Advantages of FinFET as Sensor:

Despite many references prove the already existing SiNWs efficiency as sensors, the integration with CMOS ICs and mass production is still a challenge. To achieve such integration the sensing unit architecture has to be improved and power supply constraints have to be taken into account. Additionally, the device reliability and its long-term stability have been rarely addressed.

Generally, label-free sensors provide the following advantages with respect to traditional label sensing as ELISA (Enzyme-Linked ImmunoSorbent Assay):
Better real-time detection;
More direct output and less chemical interference;
Reduced manufacturing cost;
Single-user handling, towards personal home point of care;
Highly specific and sensitive detection.

Among all label-free sensors, FETs provide the following advantages:
Best real-time detection, only surface-binding is needed for the signal transduction;
Cheapest manufacturing cost;
Mechanical durability (there are no mechanical parts);
Resistance to the environment;
Reliability over time.

Specifically Related to Fully-Depleted FinFETs, with Respect to Other ISFET Sensors, the Following Benefits are Provided:
Direct integration with electronic readout into monolithic CMOS chips with respect to other undefined SiNW sensors
High channel electrostatic control:
Absence of a variable depletion charge $\Delta Q_{dep}$ as for a standard ISFET-MOSFET
Upon scaling, steepest subthreshold slope for enhanced readout sensitivity;
Long-term stability;
High scaling compatibility;
No need for a back-gate;
Lower power consumption with respect to a ISFET:
Lower threshold voltage $V_{th}$
Lower leakage current $I_{leak}$
Smaller junction capacitance $C_j$ FIG. 3.N shows SEM (Scanning Electron Microscope) images of the FinFET implemented as sensing unit: (a) is a top view of the Si Fin at the anchor point with its contact pad, (b) and (c) are cross-sections obtained by FIB (Focused Ion Beam) showing the vertical fins with $W_{Fin}=30$ nm and $W_{Fin}=20$ nm, respectively, and aspect ratio $H_{Fin}/W_{Fin}>3$. The experimental demonstration of such a device FinFET as ionic sensor featuring (i) full pH response based on HfO$_2$ gate oxide and (ii) highly stable long-term reliability and repeatability can be found at [31-34].

V. EXPERIMENTAL DEMONSTRATION OF THE FinFET SENSOR

To perform pH measurements in a liquid environment, polytetrafluorethylen tubes were connected to a tubing pump and a valve selector system (FIG. 3.P). The liquid potential was controlled by an Ag/AgCl flow-through reference electrode included in the tubing. The first pH measurement was meant to evaluate the device threshold voltage shift, $\Delta V_{th}$, at different pH values. The FinFET drain current, $I_d$, was measured at constant source and drain voltage, $V_{ds}=80$ mV, and back-gate potential, $V_b=0$ V. The liquid potential, $V_{ref}$, was swept from 0.5 to 2.5 V, through the reference electrode at fixed pH=3. The resulting $I_d(V_{ref})$ transfer characteristic is illustrated in FIG. 8 on the left Y-axis. The liquid gate devices exhibit the same good electrical behavior as for the metal gate devices. Prior to liquid measurements, metal gate FinFETs were characterized, achieving excellent electrical properties of SS=77 mV/dec and $I_{on}/I_{off}=1.5\times10^6$ for $W_{Fin}=30$ nm, $H_{Fin}=80$ nm and $L_{Fin}=10$ μm. The right Y-axis of FIG. 8 shows the $I_d(V_g)$ corresponding to the same FinFET fabricated with a metal gate. For comparison, we set $V_{ref}=V_g+\Delta V_{sol}$, with $\Delta V_{sol}=0.75$ V. Afterwards, the valve selector system was used to exchange the solutions at different pH values. Steady-state measurements were performed between 3≤pH≤9 and the resulting $I_d(V_{ref})$ transfer characteristics are reported in FIG. 8 on the left Y-axis. For the data analysis, we can differentiate between the intrinsic sensor sensitivity, $S=V_{th}/pH$, and the readout sensitivity, $S_{out}=\Delta I_d/I_d$. While the former only depends on the oxide surface the second one is linked to the SS of the FETs as well. For all pH transitions, $S\approx56$ mV/pH is achieved. The fabricated FinFETs present full pH sensitivity and, as a consequence, sensitivity with respect to other chemicals is suppressed. Afterwards, $V_{ref}$ was fixed at 1.5 V and $I_d$ measurements vs. time were performed and reported in FIG. 9. The devices achieved a high current variation with a maximum $\Delta I_d/I_d=43\%$ for the transition pH 7→8 and averaged $\Delta I_d \approx 80$ nA/pH for 3≤pH≤8. At a different bias, $V_{ref}=2$ V, the sensor provided a maximum $\Delta I_d \approx 271$ nA/pH but the relative current variation does not exceed $\Delta I_d/I_d=28\%$. Studying in overall the current transitions we can assume a negligible background noise, with $\Delta I_d/\sigma_{\Delta Id}>60$. Tables 1 and 2 summarize the data obtained at $V_{ref}=1.5$ and $V_{ref}=2$ for each transition. The characterization of time-dependent measurements is important for fast kinetic reactions and small surface potential variation. Steady-state measurements could entail hysteretic effects affecting the detection of small $\Delta V_{th}$. According to the type of measurement the point of biasing can be adjusted for high $\Delta I_d$ or $\Delta I_d/I_d$.

The overall power consumption is of the order of tens of nW.

TABLE 1

FinFET performances as pH sensor, $V_{ref}=1.5$ V

| | FinFET, $V_{ref}=1.5$ $V_{out}$ | | | | | |
|---|---|---|---|---|---|---|
| pH | 3→4 | 4→5 | 5→6 | 6→7 | 7→8 | 3-8 |
| $S_{out}$ [%] | 29 | 33 | 40 | 40 | 43 | ≈31% |
| $\Delta I_d$ [nA] | 128 | 105 | 85 | 50 | 32 | ≈80 nA/pH |
| $\Delta I_d/\sigma_{Id}$ | 45 | 88 | 85 | 71 | 80 | ≈61 |

TABLE 2

FinFET performances as pH sensor, $V_{ref}=2$ V

| | FinFET, $V_{ref}=2$ $V_{out}$ | | | | | |
|---|---|---|---|---|---|---|
| pH | 3→4 | 4→5 | 5→6 | 6→7 | 7→8 | 3-8 |
| $S_{out}$ [%] | 9 | 7.5 | 22 | 15 | 28 | ≈14% |
| $\Delta I_d$ [nA] | 130 | 100 | 271 | 148 | 232 | ≈176 nA/pH |
| $\Delta I_d/\sigma_{Id}$ | 27 | 31 | 117 | 123 | 300 | ≈99 |

Lone-Term Stability:

The threshold voltage $V_{th}$ was monitored for 4.5 days, keeping the liquid environment at constant pH=6. Every 30 minutes the pumping system was automatically activated to renew the liquid on top of the sensors. After a stabilization time of several minutes the $I_d(V_{ref})$ characteristic was traced by sweep of the reference electrode. The $V_{th}$ was then extracted at the same $I_d=2$ nA and plotted, as shown in FIG. 10. The FinFETs behaved in an extremely stable way with a drift of $\delta V_{th}/\delta t \approx 0.13$ mV/h for single wire FinFETs with $T_{Fin}=30$ nm. The presented data also demonstrated the measurement repeatability. The $V_{th}$ measurement was, in fact, acquired more than 200 times. Assuming the intercept of a population of data equal to the mean $V_{th}$ for a specific device, its standard deviation $\sigma_{Vth} \approx 1$ mV is an indicator of the $V_{th}$ fluctuation, independent from the time drift. By subtracting the two $V_{th}$ sets of data, a residual $\Delta V_{th} \approx 0.6$ mV with its corresponding standard deviation $\sigma_{\Delta Vth} \approx 1$ mV is obtained, as shown in FIG. 11. The reliability of the FinFETs and the fabrication process was then demonstrated at the die level, since the two compared FinFETs were located at opposite sites. A small drift in time, $\delta \Delta V_{th}/\delta t \approx 0.07$ mV/h was also observed for the relative $\Delta V_{th}$.

The Final Reported Drift in Time is Demonstrated to be the Key-Advantage of the FinFET as Fabricated by the Proposed Method, with Respect to Other Structure Implemented as Sensors:

This invention: $\delta \Delta V_{th}/\delta t=0.13$ mV/h

Microsens SA [8]: $\delta \Delta V_{th}/\delta t=0.2$ mV/h

Abe et al. [9]: $\delta \Delta V_{th}/\delta t=0.3$ mV/h

The results achieved are unexpected and still not fully explained. There are probably many motivations contributing to the long-term stability: the fully immersed architecture, the uniform potential distribution and the low concentration of oxide interface traps are valid assumptions, but further investigations would be required to fully understand the phenomenon.

VI. VOLTAGE READOUT FINFET SENSOR

The FinFET sensor can be addressed by monitoring the drain current, as previously described, or by a voltage readout, as described in this section. The voltage readout provides the following advantages:

In case of sensing, the input variation, $\Delta V_{in}$, caused by a surface reaction is amplified as an output variation $\Delta V_{out}$. In first approximation the gain can be expressed as:

$$A = \left| \frac{\Delta V_{out}}{\Delta V_{in}(pH)} \right| = g_{m_{sens}} * R_{load} = \frac{g_{m_{sens}}}{g_{ds_{sens}} + g_{ds_{load}}}, \quad (1)$$

where $\Delta V_{in}$ is function of the pH solution, or other chemical species, and $R_{load}$ is the output resistance of the amplifier, given by the conductance $g_{ds}$ of the FinFETs.

In contrast to an exponential current FET readout, the voltage variation readout here proposed is expected to be linear as well as more favourable in terms of signal processing and noise tolerance. This holds especially for biosensors where current variations are usually very small.

Moreover, if the FinFET with metal gate is a depletion-mode transistor, i.e. normally-on at $V_g=0$ V: (i) the output voltage can be as high as the power supply, $V_{DD}$, and (ii) the slope of the $V_{out}(V_{in})$ characteristic is very steep in the transition region.

An experimental demonstration of the amplification principle has been realized by the connection of a fully-immersed liquid gate FinFET and a metal gate FinFET, both n-MOS devices. FIG. 12 illustrates the device concept, while FIG. 13 shows the practical realization with the circuit schematic.

However, the proposed principle does not depend on its physical realization which could also be achieved by other layout, implementing single or monolithic FinFET units.

The amplifying stage has been tested in a liquid environment for different pH values. The result is shown in FIG. 14, while Table III summarizes the characteristics of each pH transition.

TABLE 3

FinFET sensor, voltage readout performances

| pH | FinFETS-based Amplifier | | | | | |
|---|---|---|---|---|---|---|
| | 3→4 | 4→5 | 5→6 | 6→7 | 7→8 | 3-8 |
| $\Delta V_{in}$[mV] | 30 | 6 | 27 | 5 | 16 | ≈17 mV/pH |
| $\Delta V_{out}$[mV] | 185 | 40 | 174 | 31 | 102 | ≈107 mV/pH |
| $A = \Delta V_{in}/\Delta V_{out}$ | 6.2 | 6.6 | 6.5 | 6.2 | 6.4 | ≈6.4 |

Each $V_{out}(V_{ref})$ curve exhibits a gain A>6, with an average gain A≈6.4. The maximum $\Delta V_{out}$=185/pH mV is achieved between pH 3→4, and an overall $\Delta V_{out}$ β107 mV/pH is averaged over pH 3 to 8. The $\Delta V_{out}$/pH has been calculated at $V_{ref}$=1.56 V, where the inverter slope is constant over the whole pH range. Due to the voltage-to-voltage transduction and by choosing a suitable $V_{ref}$, the gain can be kept constant and independent from the different $\Delta V_{in}$/pH values. This aspect is important for sensors that do not exhibit a nernstian pH response, which leads to nonlinear $\Delta V_{in}$/pH.

VII. OUTLOOK: POTENTIAL DIAGNOSTIC APPLICATIONS

Some potential applications of the FinFET sensor are:

Single-cell analysis: Blood analyses are normally performed by centrifugation of millions of red blood cells, causing the loss of information by sub-population, which may become sick. On the other hand, the single-cell approach consists in analyzing a large number of individual cells and determining the distribution of cellular properties [43, 44]. The identification of abnormalities in sub-groups turns out to be a hallmark of physiology and pathology [45]. For example, sickle cell anemia is a blood disorder characterized by an abnormal, rigid, sickle shape of the red blood cells. The abnormal cells can obstruct capillaries and restrict blood flow to an organ, resulting in ischemia, pain, necrosis and often organ damage. If promptly detected, the effects of the diseases may be contained and life expectancy increased. It is also known, that the cytosol composition of such cells is different than that of the healthy ones, especially the concentration of sodium and calcium [46]. Lee et al. [47] have proposed a lysis method for opening the cells based on a PDMS array with holes able to contain only one cell. Under an electromagnetic field at a specific frequency applied through the electrodes locally deposited (electrophoresis), the cells are opened up and the cytosol components are analyzed by fluorescence. Such label-die method can be substituted by the direct analysis of the cytosol components by the FinFET fabricated on a Si substrate and aligned with the PDMS trapping array. The FinFETs would have the double use of electrophoresis tools and sensors, as illustrated in FIG. 6.

Intra-body monitoring: A CMOS readout chip integrating the FinFET sensors could be applied for monitoring the pH or other chemical species of blood. Continuous intraarterial blood pH monitoring is, in fact, highly desirable in clinical practice [8], either during anesthesia in major surgery (at least 10 hours) or for postoperative monitoring (several days) [7]. However, devices with appreciable accuracy are still not commercially available to date and arterial blood samples are usually drawn intermittently and analyzed by a conventional blood gas analyzer (BGA). Several limitations are associated with intermittent blood sampling [35]. The accuracy should be maintained within ±0.02 pH, without the need for recalibration. For example, the change in hydrogen ions is directly connected to the onset of angina and electrocardiographic abnormalities in ischaemic patients [36]. The monitoring of the intra-gastric pH also represents an interesting application field. Acid related diseases are often chronic, underinvestigated and overtreated [37]. The gastric acid output (GAO) can be continuously monitored to address such diseases, but the lack of a non-invasive, accurate and reproducible tool have slowed down its clinical use. Recently, a first attempt of continuous and real-time monitoring has been provided by catheter-free pills integrating a pH sensor attached to the esophagus, which wirelessly transmit the data to a small recorder [38,39]. However, differences between old 24-hour catheter pH systems and these new methods have been reported [40,41] making this field open for investigation and improvement.

New patterns for health control: A recent field of research is focusing on the chemical information contained in the human sweat or saliva, which are more accessible than blood. For example, the sodium concentration contained in the sweat and sweat rate could be used to indicate the proper time to hydrate during physical exercise and avoid the risk of muscle cramps. In [42], a rapid colorimetric detection of pH in sweat and saliva is proposed. FET devices could be used for more precise and direct analysis in order to validate the correlation between pH and critical health status such as dehydration, in case of sweat, or enamel decalcification, an acidic breakdown of calcium in the teeth, in case of saliva. Wearable devices for athletes could integrate such monitoring functions.

VIII. REFERENCES

1. M. Law, J. Goldberger, and P. Yang, "Semiconductor nanowires and nanotubes," Annu. Rev. Mater. Res., vol. 34, pp. 83-122, 2004.
2. D. Hisamoto, T. Kaga, Y. Kawamoto, and E. Takeda, "A fully depleted lean-channel transistor (DELTA)—a novel vertical ultra thin SOIMOSFET," in Electron Devices Meeting, 1989, IEDM '89. Technical Digest., International, 1989, pp. 833-836.
3. X. Huang, W.-C. Lee, C. Kuo, D. Hisamoto, L. Chang, J. Kedzierski, E. Anderson, H. Takeuchi, Y.-K. Choi, K. Asano et al., "Sub 50-nm FinFET: PMOS," in Electron Devices Meeting, 1999. IEDM'99. Technical Digest. International, 1999, pp. 67-70.
4. J. P. Colinge, FinFETs and Other Multi-Gate Transistors. Springer, 2008.
5. G. E. Moore, "Progress in digital integrated electronics," in Electron Devices Meeting, 1975 International, vol. 21, 1975, pp. 11-13.
6. J. P. Colinge, Silicon-On-Insulator technology: Materials to VLSI, 2nd Edition. Kluwer Academic Publishers, 1997.
7. P. Bergveld and A. Sibbald, Analytical and biomedical applications of ion-selective field effect transistors. Elsevier Amsterdam, 1988, vol. 23.
8. Microsens. Ion sensitive field effect transistor-isfet. [Online]. Available: http://www.microsens.ch/products/chemical.htm.

9. H. Abe, M. Esashi, and T. Matsuo, "ISFET's using inorganic gate thin films," Electron Devices, IEEE Transactions on, vol. 26, no. 12, pp. 1939-1944, 1979.
10. J. Lee, J.-M. Lee, J. H. Lee, W. H. Lee, M. Uhm, B.-G. Park, D. M. Kim, Y.-J. Jeong, and D. H. Kim, "Complementary Silicon Nanowire Hydrogen Ion Sensor With High Sensitivity and Voltage Output," Electron Device Letters, IEEE, vol. 33, no. 12, pp. 1768-1770, 2012.
11. I. Park, Z. Li, A. P. Pisano, and R. S. Williams, "Top-down fabricated silicon nanowire sensors for real-time chemical detection," Nanotechnology, vol. 21, no. 1, p. 015501, 2010.
12. S. K. Yoo, S. Yang, and J.-H. Lee, "Hydrogen Ion Sensing Using Schottky Contacted Silicon Nanowire FETs," Nanotechnology, IEEE Transactions on, vol. 7, no. 6, pp. 745-748, 2008.
13. S. Kim, T. Rim, K. Kim, U. Lee, E. Baek, H. Lee, C.-K. Baek, M. Meyyappan, M. J. Deen, and J.-S. Lee, "Silicon nanowire ion sensitive field effect transistor with integrated Ag/AgCl electrode: pH sensing and noise characteristics," Analyst, vol. 136, pp. 5012-5016, 2011.
14. J.-H. Ahn, J.-Y. Kim, M.-L. Seol, D. J. Baek, Z. Guo, C.-H. Kim, S.-J. Choi, and Y.-K. Choi, "A pH sensor with a double-gate silicon nanowire field-effect transistor," Applied Physics Letters, vol. 102, no. 8, p. 083701, 2013.
15. J.-H. Ahn, J.-Y. Kim, K. Choi, D.-I. Moon, C.-H. Kim, M.-L. Seol, T. J. Park, S. Y. Lee, and Y.-K. Choi, "Nanowire FET Biosensors on a Bulk Silicon Substrate," Electron Devices, IEEE Transactions on, vol. 59, no. 8, pp. 2243-2249, 2012.
16. X. T. Vu, J. F. Eschermann, R. Stockmann, R. Ghosh-Moulick, A. Offenhausser, and S. Ingebrandt, "Top-down processed silicon nanowire transistor arrays for biosensing," physica status solidi (a), vol. 206, no. 3, pp. 426-434, 2009.
17. Y. Cui, Q. Wei, H. Park, and C. M. Lieber, "Nanowire Nanosensors for Highly Sensitive and Selective Detection of Biological and Chemical Species," Science, vol. 293, no. 5533, pp. 1289-1292, 2001.
18. A. Tarasov, M. Wipf, R. L. Stoop, K. Bedner, W. Fu, V. A. Guzenko, O. Knopfmacher, M. Calame, and C. Schönenberger, "Understanding the Electrolyte Background for Biochemical Sensing with Ion-Sensitive Field-Effect Transistors," ACS Nano, vol. 6, no. 10, pp. 9291-9298, 2012.
19. Y. Chen, X. Wang, S. Erramilli, P. Mohanty, and A. Kalinowski, "Silicon-based nanoelectronic field-effect pH sensor with local gate control," Applied Physics Letters, vol. 89, no. 22, p. 223512, 2006.
20. G.-J. Zhang, J. H. Chua, R.-E. Chee, A. Agarwal, S. M. Wong, K. D. Buddharaju, and N. Balasubramanian, "Highly sensitive measurements of PNA-DNA hybridization using oxide-etched silicon nanowire biosensors," Biosensors and Bioelectronics, vol. 23, no. 11, pp. 1701-1707, 2008.
21. Z. Li, Y. Chen, X. Li, T. I. Kamins, K. Nauka, and R. S. Williams, "Sequence-Specific Label-Free DNA Sensors Based on Silicon Nanowires," Nano Letters, vol. 4, no. 2, pp. 245-247, 2004.
22. J.-i. Hahmand C. M. Lieber, "Direct ultrasensitive electrical detection of DNA and DNA sequence variations using nanowire nanosensors," Nano Letters, vol. 4, no. 1, pp. 51-54, 2004.
23. Stern, E.; Vacic, A.; Reed, Mark A., "Semiconducting Nanowire Field-Effect Transistor Biomolecular Sensors," Electron Devices, IEEE Transactions on, vol. 55, no. 11, pp. 3119, 3130, November 2008
24. J.-I. Hahmand C. M. Lieber, "Direct ultrasensitive electrical detection of DNA and DNA sequence variations using nanowire nanosensors," Nano Letters, vol. 4, no. 1, pp. 51-54, 2004.
25. G. Zheng, F. Patolsky, Y. Cui, W. U. Wang, and C. M. Lieber, "Multiplexed electrical detection of cancer markers with nanowire sensor arrays," Nature biotechnology, vol. 23, no. 10, pp. 1294-1301, 2005.
26. A. Kim, C. S. Ah, H. Y. Yu, J.-H. Yang, I.-B. Baek, C.-G. Ahn, C.-W. Park, M. S. Jun, and S. Lee, "Ultrasensitive, label-free, and real-time immunodetection using silicon field effect transistors," Applied Physics Letters, vol. 91, no. 10, p. 103901, 2007.
27. C. Li, M. Curreli, H. Lin, B. Lei, F. Ishikawa, R. Datar, R. J. Cote, M. E. Thompson, and C. Zhou, "Complementary detection of prostate-specific antigen using In2O3 nanowires and carbon nanotubes," Journal of the American Chemical Society, vol. 127, no. 36, pp. 12 484-12 485, 2005.
28. W. U. Wang, C. Chen, K.-H. Lin, Y. Fang, and C. M. Lieber, "Label-free detection of small-molecule-protein interactions by using nanowire nanosensors," Proceedings of the National Academy of Sciences of the United States of America, vol. 102, no. 9 pp. 3208-3212, 2005.
29. G.-J. Zhang, L. Zhang, M. J. Huang, Z. H. H. Luo, G. K. I. Tay, E.-J. A. Lim, T. G. Kang, and Y. Chen, "Silicon nanowire biosensor for highly sensitive and rapid detection of Dengue virus," Sensors and Actuators B: Chemical, vol. 146, no. 1, pp. 138-144, 2010.
30. P.-L. Chiang, T.-C. Chou, T.-H. Wu, C.-C. Li, C.-D. Liao, J.-Y. Lin, M.-H. Tsai, C.-C. Tsai, C.-J. Sun, C.-H. Wang, J.-M. Fang, and Y.-T. Chen, "Nanowire Transistor-Based Ultrasensitive Virus Detection with Reversible Surface Functionalization," Chemistry Asian Journal, vol. 7, no. 9, pp. 2073-2079, 2012.
31. S. Rigante, P. Scarbolo, D. Bouvet, M. Wipf, A. Tarasov, K. Bedner, and A. M. Ionescu, "High-k dielectric FinFETs towards sensing integrated circuits", in Proceedings of Ultimate Integration on Silicon (ULIS), 14th International Conference on, vol. 73, no. 76, pp. 19-21, Warwick University, Coventry, United Kingdom, 2013
32. S. Rigante, M. Wipf, A. Tarasov, D. Bouvet, K. Bedner, R. L. Stoop, and A. M. Ionescu, "Integrated FinFET based sensing in a liquid environment", in Proceedings of Solid-State Sensors, Actuators and Microsystems (TRANSDUCERS EUROSENSORS XXVII): The 17th International Conference on, pp. 681-684, Barcelona, Spain, 2013
33. S. Rigante, P. Livi, M. Wipf, K. Bedner, D. Bouvet, A. Bazigos, A. Rusu, A. Hierlemann and A. M. Ionescu, "Low Power FinFET pH-Sensor with High-Sensitivity Voltage Readout", in Proceedings of the European Solid-State Device Research Conference (ESSDERC), IEEE, Bucharest, Romania, 2013
34. S. Rigante, M. Wipf, G. Navarra, A. Bazigos, K. Bedner, D. Bouvet and A. M. Ionescu, "FinFET with Fully pH-Responsive HfO2 as Highly Stable Biochemical Sensor", in Proceedings of IEEE Micro ElectroMechanical Systems, MEMS'2014, San Francisco, Calif., United States, 2014
35. B. E. Smith, P. H. King, and L. Schlain, "Clinical evaluation-continuous real-time intraarterial blood gas-monitoring during anesthesia and surgery by fiber optic sensor," International journal of clinical monitoring and computing, vol. 9, no. 1, pp. 45-52, 1992.
36. S. Cobbe and P. Poole-Wilson, "Continuous coronary sinus and arterial pH monitoring during pacing-induced 36. ischaemia in coronary artery disease," British heart journal, vol. 47, no. 4, pp. 369-374, 1982.
37. S. R. Majumdar, S. B. Soumerai, F. A. Farraye, M. Lee, J. A. Kemp, J. M. Henning, P. Schrammel, R. F. LeCates, and D. Ross-Degnan, "Chronic acid-related disorders are common and underinvestigated," The American journal of gastroenterology, vol. 98, no. 11, pp. 2409-2414, 2003.
38. D. Weinstein, S. Derijke, C. Chow, L. Foruraghi, X. Zhao, E. Wright, M. Whatley, R. Maass-Moreno, C. Chen, and S. Wank, "A new method for determining gastric acid output using a wireless pH-sensing capsule," Alimentary pharmacology & therapeutics, 2013.
39. B. E. Lacy, T. O'Shana, M. Hynes, M. L. Kelley, J. E. Weiss, L. Paquette, and R. I. Rothstein, "Safety and tolerability of transoral Bravo capsule placement after transnasal manometry using a validated conversion factor," The American journal of gastroenterology, vol. 102, no. 1, pp. 24-32, 2007.
40. J. E. Pandolfino, Q. Zhang, M. A. Schreiner, S. Ghosh, M. P. Roth, and P. J. Kahrilas, "Acid reflux event detection using the Bravo wireless versus the Slimline catheter pH systems: why are the numbers so different?" Gut, vol. 54, no. 12, pp. 1687-1692, 2005.
41. W.-M. Wong, J. Bautista, R. Dekel, I. Malagon, I. Tuchinsky, C. Green, R. Dickman, R. Esquivel, and R. Fass, "Feasibility and tolerability of transnasal/per-oral placement of the wireless pH capsule vs. traditional 24-h oesophageal pH monitoring—a randomized trial," Alimentary pharmacology & therapeutics, vol. 21, no. 2, pp. 155-163, 2005.
42. V. Oncescu, D. O'Dell, and D. Erickson, "Smartphone based health accessory for colorimetric detection of biomarkers in sweat and saliva," Lab Chip, vol. 13, pp. 3232-3238, 2013.
43. Y. Tokimitsu, H. Kishi, S. Kondo, R. Honda, K. Tajiri, K. Motoki, T. Ozawa, S. Kadowaki, T. Obata, S. Fujiki, C. Tateno, H. Takaishi, K. Chayama, K. Yoshizato, E. Tamiya, T. Sugiyama, and A. Muraguchi, "Single lymphocyte analysis with amicrowell array chip," Cytometry Part A, vol. 71A, no. 12, pp. 1003-1010, 2007.
44. A. Jin, T. Ozawa, K. Tajiri, T. Obata, S. Kondo, K. Kinoshita, S. Kadowaki, K. Takahashi, T. Sugiyama, H. Kishi et al., "A rapid and efficient single-cell manipulation method for screening antigen-specific antibody-secreting cells from human peripheral blood," Nature medicine, vol. 15, no. 9, pp. 1088-1092, 2009.
45. B. F. Brehm-Stecher and E. A. Johnson, "Single-cell microbiology: tools, technologies, and applications," Microbiology and molecular biology reviews, vol. 68, no. 3, pp. 538-559, 2004.
46. L. Tamer, G. Polat, G. Yücebilgi., B. Güven., and F. Ba,slami,shi, "The levels of sera malondialdehyde, erythrocytemembrane Na+-K+/Mg++ and Ca++/Mg++ adenosine 5'triphosphatase in patients with sickle cell anemia," Turk J Haematol, vol. 17, pp. 23-6, 2000.
47. W. C. Lee, S. Rigante, A. P. Pisano, and F. A. Kuypers, "Large-scale arrays of picoliter chambers for single-cell analysis of large cell populations," Lab Chip, vol. 10, pp. 2952-2958, 2010.

The invention claimed is:

1. A method of producing a FinFET sensor device comprising the steps of:
    providing a silicon substrate;
    etching the silicon substrate to produce at least one upwardly extending Fin structure externally protruding from a surface of the silicon substrate;
    depositing a spacer layer on the at least one Fin structure;
    etching a section of the spacer layer to expose the underlying silicon;
    isotropic etching of the exposed silicon surrounding the at least one Fin structure; and
    carrying out oxidation of the silicon surrounding the at least one upwardly extending Fin structure to produce a Fin structure of silicon that is detached and isolated from the silicon substrate and inside the at least one upwardly extending Fin structure.

2. The method according to claim 1, wherein the silicon substrate solely comprises silicon.

3. The method according to claim 1, further comprising:
    depositing a stress reducing layer on the at least one Fin structure before depositing a spacer layer on the at least one Fin structure.

4. The method according to claim 1, further comprising:
    providing a source and drain electrode.

5. A FinFET sensor device produced by the method according to claim 1.

6. A method of producing a three dimensional stack of FinFET sensor devices comprising the steps of:
    providing a silicon substrate;
    etching the silicon substrate to produce at least one upwardly extending Fin structure externally protruding from a surface of the silicon substrate;
    alternately depositing first and second layers on top of each other so as to enclose the at least one upwardly extending Fin structure;
    etching at least one aperture through the first and second layer stack to create an oxidation cavity; and
    carrying out oxidation in the oxidation cavity to produce a plurality of stacked individual silicon regions in the at least one upwardly extending Fin structure;
    etching to remove the first and second layer stack and to expose each individual silicon region of the plurality of stacked individual silicon regions in the at least one upwardly extending Fin structure; and
    providing source and drain electrodes.

7. The method according to claim 6, wherein the silicon substrate is a bulk silicon substrate solely comprises silicon.

8. A three dimensional stack of FinFET sensor devices produced by the method according to claim 6.

9. Sensing apparatus including the three dimensional stack of FinFET sensor devices according claim 8, and a liquid, gas or solid to be sensed.

10. The method according to claim 1, wherein the etching of the section of the spacer layer to expose the underlying silicon is carried out using isotropic or anisotropic etching.

11. The method according to claim 1, wherein the carrying out the oxidation produces a Fin structure of silicon that is fully detached and fully isolated from the silicon substrate and inside the at least one upwardly extending Fin structure.

12. The method according to claim 6, wherein carrying out the oxidation produces the plurality of stacked individual silicon regions so that the plurality of stacked individual silicon regions are separated from each other by an oxidized region.

13. The method according to claim 12, wherein carrying out the etching to remove the first and second layer stack also removes the oxidized regions to expose the plurality of individual silicon regions in the at least one upwardly extending Fin structure.

14. The method according to claim 6, wherein each individual silicon region of the exposed plurality of stacked individual silicon regions defines a Fin structure and a thickness of the deposited first layer defines the Fin structure height, and wherein a thickness of the deposited second layer defines a separation distance between said Fin structures.

15. The method according to claim 14, wherein the etching the silicon substrate is carried out to produce a plurality of upwardly extending Fin structures externally protruding from a surface of the silicon substrate,
   wherein the alternately deposited first and second layers enclose the plurality of upwardly extending Fin structures,
   wherein the at least one aperture is a plurality of apertures etched through the first and second layer stack to create a plurality of oxidation cavities,
   wherein the oxidation is carried out in the plurality of oxidation cavities to produce a plurality of resulting upwardly extending Fin structures each including a plurality of stacked individual silicon regions, and
   wherein the etching is carried out to remove the first and second layer stack and to expose each individual silicon region of the plurality of upwardly extending Fin structures to define a plurality of individual silicon regions for a three dimensional sensor array.

16. The method according to claim 15, wherein the etching is carried out to remove the first and second layer stack and to remove oxidized regions between the individual silicon regions.

17. The method according to claim 6, wherein oxidation in the oxidation cavity produces a plurality of stacked individual silicon regions, each individual silicon region being fully detached and fully isolated from the silicon substrate.

* * * * *